United States Patent
Fujiwara et al.

(10) Patent No.: US 9,237,994 B2
(45) Date of Patent: *Jan. 19, 2016

(54) GLASS FLAKE AND COATED GLASS FLAKE

(75) Inventors: Kosuke Fujiwara, Tokyo (JP); Akihiro Koyama, Tokyo (JP)

(73) Assignee: NIPPON SHEET GLASS COMPANY, LIMITED, Tokyo (JP)

(*) Notice: Subject to any disclaimer, the term of this patent is extended or adjusted under 35 U.S.C. 154(b) by 284 days.

This patent is subject to a terminal disclaimer.

(21) Appl. No.: 13/058,090

(22) PCT Filed: Aug. 26, 2009

(86) PCT No.: PCT/JP2009/064846
§ 371 (c)(1),
(2), (4) Date: Feb. 8, 2011

(87) PCT Pub. No.: WO2010/024283
PCT Pub. Date: Mar. 4, 2010

(65) Prior Publication Data
US 2011/0151261 A1  Jun. 23, 2011

(30) Foreign Application Priority Data
Aug. 27, 2008  (JP) ................. 2008-217729

(51) Int. Cl.
*B32B 17/00* (2006.01)
*C03C 3/087* (2006.01)
(Continued)

(52) U.S. Cl.
CPC ... *A61K 8/25* (2013.01); *A61K 8/02* (2013.01); *A61K 8/19* (2013.01); *A61K 8/26* (2013.01);
(Continued)

(58) Field of Classification Search
None
See application file for complete search history.

(56) References Cited

U.S. PATENT DOCUMENTS

| 4,249,946 | A | 2/1981 | Danielson |
| 7,166,549 | B2 * | 1/2007 | Fechner et al. ........... 501/56 |

(Continued)

FOREIGN PATENT DOCUMENTS

| EP | 1865031 A1 | 12/2007 |
| EP | 2287124 A1 | 2/2011 |

(Continued)

OTHER PUBLICATIONS

Machine translation JP 11-060270. (1999).*

(Continued)

*Primary Examiner* — Alexandre Ferre
(74) *Attorney, Agent, or Firm* — Seager, Tufte & Wickhem LLP

(57) ABSTRACT

A glass flake (10) having improved heat resistance and chemical resistance is formed from a glass base material satisfying, in mass %, $60 \leq SiO_2 \leq 75$, $5 < Al_2O_3 \leq 15$, $3 \leq CaO \leq 20$, $6 \leq Na_2O \leq 20$ and $9 \leq (Li_2O+Na_2O+K_2O) \leq 13$. When $9 \leq (Li_2O+Na_2O+K_2O) \leq 13$ is satisfied in mass %, the CaO content and the $Na_2O$ content are preferably set within the ranges of $5 \leq CaO \leq 20$ and $6 \leq Na_2O \leq 13$, respectively. When $13 \leq (Li_2O+Na_2O+K_2O) \leq 20$ is satisfied in mass %, the CaO content and the Na2O content are preferably set within the ranges of $3 \leq CaO \leq 15$ and $9 \leq Na_2O \leq 20$, respectively. The working temperature of the glass base material is preferably 1180° C.-1300° C. The temperature difference ΔT obtained by taking the devitrification temperature of the glass base material from the working temperature of the glass base material is preferably 0° C.-200° C. The glass transition temperature of the glass base material is preferably 550° C.-700° C. The acid resistance index ΔW of the glass base material is preferably 0.05-1.5 mass %.

18 Claims, 4 Drawing Sheets

(51) Int. Cl.
- C03C 3/091 (2006.01)
- C03C 6/04 (2006.01)
- C03B 37/005 (2006.01)
- A61K 8/25 (2006.01)
- A61K 8/02 (2006.01)
- A61K 8/19 (2006.01)
- A61K 8/26 (2006.01)
- A61K 8/29 (2006.01)
- A61Q 1/02 (2006.01)
- A61Q 1/06 (2006.01)
- A61Q 1/10 (2006.01)
- A61Q 1/12 (2006.01)
- A61Q 3/02 (2006.01)
- C03C 12/00 (2006.01)
- C03C 17/06 (2006.01)
- C03C 17/23 (2006.01)
- C09C 1/00 (2006.01)

(52) U.S. Cl.
CPC ... *A61K 8/29* (2013.01); *A61Q 1/02* (2013.01); *A61Q 1/06* (2013.01); *A61Q 1/10* (2013.01); *A61Q 1/12* (2013.01); *A61Q 3/02* (2013.01); *C03C 3/087* (2013.01); *C03C 12/00* (2013.01); *C03C 17/06* (2013.01); *C03C 17/23* (2013.01); *C09C 1/0018* (2013.01); *C09C 1/0021* (2013.01); *A61K 2800/436* (2013.01); *C09C 2200/102* (2013.01); *C09C 2200/301* (2013.01); *Y10T 428/2982* (2015.01); *Y10T 428/2996* (2015.01)

(56) References Cited

U.S. PATENT DOCUMENTS

| | | | |
|---|---|---|---|
| 7,285,508 B2 * | 10/2007 | Fujiwara et al. | 501/33 |
| 2006/0048679 A1 * | 3/2006 | Fujiwara et al. | 106/482 |
| 2008/0063728 A1 * | 3/2008 | Fechner et al. | 424/618 |
| 2010/0183737 A1 * | 7/2010 | Fujiwara et al. | 424/613 |

FOREIGN PATENT DOCUMENTS

| | | |
|---|---|---|
| JP | 63147843 | 6/1988 |
| JP | 03-040938 A | 2/1991 |
| JP | 03-076642 A | 4/1991 |
| JP | 07-025635 A | 1/1995 |
| JP | 11-029344 A | 2/1999 |
| JP | 11-060270 A | 3/1999 |
| JP | 11-263629 A | 9/1999 |
| JP | 2001213639 | 8/2001 |
| JP | 2007-145699 A | 6/2007 |
| JP | 2007-145700 A | 6/2007 |
| WO | WO 2007148758 A1 * | 12/2007 |

OTHER PUBLICATIONS

"International Preliminary Report on Patentability for International Application No. PCT/JP2009/064846," International Filing Date of Aug. 26, 2009, Report Completed by Authorized Officer of the International Bureau. 5 pages.

Wang et al., "Manufacturing Process of Glass", Press of Chemistry Industry, edition 1, pp. 84 and 250.

* cited by examiner

GLASS FLAKE AND COATED GLASS FLAKE

TECHNICAL FIELD

The present invention relates to glass flakes and coated glass flake blended with, for example, resin compositions, paint, ink, cosmetics, and the like to obtain superior color tones and luster.

BACKGROUND ART

When such glass flakes are dispersed in, for example, a resin composition (resin matrix), a resin mold product obtained from the resin composition will have increased strength and dimensional accuracy. Further, glass flakes are blended with paint and applied to metal or concrete surfaces as lining. The glass flakes have a metallic color produced by coating their surfaces with a metal. Further, the surfaces of the glass flakes may be coated by a metal oxide to produce an interference color resulting from interference of reflection light. In this manner, glass flakes coated by a metal coating or a metal oxide coating is preferable for use as a luster pigment. Luster pigment using such glass flakes is preferably used for applications in which the color tone and luster are important, such as paint and cosmetics.

A glass flake is fabricated by inflating a molten glass base material with an injection nozzle to form a balloon-shaped hollow glass film and then crushing the hollow glass film with a pressing roller, for example. When such a fabrication process is taken into account, it is required that glass flakes have superior meltability, satisfactory formability, a suitable temperature-viscosity property, and a devitrification temperature that is lower than the working temperature. The working temperature is the temperature when the viscosity of glass is 100 Pa·s (1000 P). Further, the devitrification temperature is the temperature at which crystals form and start to grow in the molten glass base material.

For the temperature-viscosity property, it is preferable that the working temperature be less than or equal to 1300° C. since the glass flakes become difficult to form, particularly, when the working temperature becomes too high. A lower working temperature for glass decreases the cost of fuel when melting the glass crude material. This also decreases the thermal damage caused to a kiln or fabrication apparatus of the glass flakes and thereby allows for the kiln or fabrication apparatus to have a longer life.

Further, when forming a metal coating or a metal oxide coating on the surface of glass flakes, the glass flakes may undergo a high-temperature treatment. Additionally, glass flakes or coated glass flakes may be blended with paint and undergo a high-temperature treatment for applications such as baking finishing. Accordingly, glass flakes require sufficient heat resistance. Soda-lime glass, which is typically used as a so-called sheet glass composition, contains a large amount of alkali metal oxide and does not have sufficient heat resistance. When considering the application of glass flakes blended with paint or cosmetics, a coating film or coating would require acid resistance, alkali resistance, and the like. Hence, the glass flakes would require high chemical durability.

To meet these requirements, the applicant of the present application has suggested glass flakes that will now be described. For example, patent document 1 listed below suggests glass flakes that specify the content of silicon dioxide ($SiO_2$), the total content of silicon dioxide and aluminum oxide ($Al_2O_3$), the total content of magnesium oxide (MgO) and calcium oxide (CaO), and the total content of lithium oxide ($Li_2O$), sodium oxide ($Na_2O$), and potassium oxide ($K_2O$).

Patent document 2 listed below suggests glass flakes that specify the content of silicon dioxide, the total content of oxide magnesium and calcium oxide, the total content of lithium oxide and sodium oxide, and the content of titanium dioxide ($TiO_2$).

PRIOR ART DOCUMENTS

Patent Document 1: Japanese Laid-Open Patent Publication No. 2007-145699
Patent Document 2: Japanese Laid-Open Patent Publication No. 2007-145700

DISCLOSURE OF THE INVENTION

Problems that are to be Solved by the Invention

Silicon dioxide and aluminum oxide are components used to form the skeleton for glass. When the content of silicon dioxide and aluminum oxide are insufficient, the glass transition temperature does not become high, and the heat resistance is insufficient. Further, silicon dioxide has a tendency to increase acid resistance, while aluminum oxide has a tendency to decrease acid resistance. Thus, the balance of silicon dioxide and aluminum oxide is important. Magnesium oxide and calcium oxide are components that adjust the devitrification temperature and viscosity of glass in a satisfactory manner.

However, patent documents 1 and 2 disclose that the content of aluminum oxide is preferably 5% or less. In the described examples, the content of aluminum oxide is 3.20 percent by mass or less in patent document 1 and 4.84 percent by mass or less in patent document 2. In patent documents 1 and 2, the content of silicon dioxide is set to be excessive in comparison with the content of aluminum oxide. Thus, the glass flakes have insufficient heat resistance. Further, chemical durability, such as water resistance, is also decreased.

In addition, in the glass flakes described in patent document 1, the working temperature is set to 1170° C. or less. In the glass flakes described in patent document 2, the working temperature is set to less than 1200° C. Accordingly, when the decrease in temperature of glass becomes large during fabrication of the glass flakes, the plasticity of glass decreases, and it becomes difficult to obtain glass fakes having a uniform thickness.

It is an object of the present invention to provide glass flakes having uniform thickness and coated glass flakes that have improved heat resistance and chemical durability.

Means for Solving the Problems

The inventors of the present invention have conducted studies on a preferable glass composition for glass flakes to achieve the above object. As a result, the inventors have found that glass flakes having improved heat resistance, chemical durability (in particular, acid resistance), and formability are obtained by controlling the contents of silicon dioxide ($SiO_2$) and aluminum oxide ($Al_2O_3$) and by controlling the total content of alkali metal oxides ($Li_2O+Na_2O+K_2O$). In particular, the inventors have found that the contents of CaO and $Na_2O$ should be respectively set to $5 \leq CaO \leq 20$ and $6 \leq Na_2O \leq 13$ when $9 \leq (Li_2O+Na_2O+K_2O) \leq 13$ is satisfied and that the contents of CaO and $Na_2O$ should be respectively set to $3 \leq CaO \leq 15$ and $9 \leq Na_2O \leq 20$ when $13 < (Li_2O+Na_2O+K_2O)$ ≤20 is satisfied. The inventors have also found that the setting of a working temperature range for the glass base material that forms the glass flakes obtains glass flakes with further even thickness. This completed the invention.

More specifically, a first aspect of the present invention is a glass flake being characterized in that the glass flake is formed from a glass base material having a composition expressed in percent by mass of:

$60 \leq SiO_2 \leq 75$;

$5 < Al_2O_3 \leq 15$;

$3 \leq CaO \leq 20$;

$6 \leq Na_2O \leq 20$; and $9 \leq (Li_2O+Na_2O+K_2O) \leq 200$.

In one example, when the composition of the glass base material satisfies $9 \leq (Li_2O+Na_2O+K_2O) \leq 13$ as expressed in percent by mass, CaO and $Na_2O$ contents are set to:

$5 \leq CaO \leq 20$; and $6 \leq Na_2O \leq 13$.

In one example, when $13 < (Li_2O+Na_2O+K_2O) \leq 20$ as expressed in percent by mass is satisfied, the contents of CaO and $Na_2O$ are set to:

$3 \leq CaO \leq 15$; and $9 \leq Na_2O \leq 20$.

In one example, a working temperature for the glass base material is 1180° C. to 1300° C.

In one example, a temperature difference ΔT obtained by subtracting a devitrification temperature from a working temperature of the glass base material is 0° C. to 200° C.

In one example, a glass transition temperature of the glass base material is 550° C. to 700° C.

In one example, ΔW, which is an index for acid resistance of the glass base material, is 0.05 to 1.5 percent by mass.

One aspect of the present invention is a coated glass flake being characterized by the glass flake according to the first aspect and a coating that covers a surface of the glass flake, the coating having a main component of metal or metal oxide.

The glass base material that forms the glass flake according to the first aspect of the present invention is set to satisfy $60 \leq SiO_2 \leq 75$ and $5 < Al_2O_3 \leq 15$. This ensures that the contents of silicon dioxide and aluminum oxide are sufficient and that silicon dioxide and aluminum oxide sufficiently function to form the skeleton for glass. Further, the glass transition temperature is high, the meltability is high, and the acid resistance and water resistance may be increased. Further, the contents of calcium oxide and sodium oxide are set to $3 \leq CaO \leq 20$ and $6 \leq Na_2O \leq 20$. Thus, the devitrification temperature and viscosity during glass formation are satisfactory. Moreover, the total amount of lithium oxide, sodium oxide, and potassium oxide is set to $9 \leq (Li_2O+Na_2O+K_2O) \leq 20$. In this manner, the contents of alkali metal oxides are sufficient, and the devitrification temperature and viscosity during glass formation are satisfactory. Since the glass flake is formed from glass base material having the above composition, the heat resistance and chemical durability of the glass flake is improved.

In particular, by setting the contents of CaO and $Na_2O$ to $5 \leq CaO \leq 20$ and $6 \leq Na_2O \leq 13$ when $9 \leq (Li_2O+Na_2O+K_2O) \leq 13$ is satisfied and by setting the contents of CaO and $Na_2O$ to $3 \leq CaO \leq 15$ and $9 \leq Na_2O \leq 20$ when $13 < (Li_2O+Na_2O+K_2O) \leq 20$ is satisfied, a glass flake that is easier to mold is obtained.

When the working temperature for the glass base material is 1180° C. to 1300° C., an increase in the viscosity and a decrease in the plasticity that would be caused by a decrease in the glass temperature are suppressed, and the glass flake is formed to have an even thickness.

When the temperature difference ΔT obtained by subtracting the devitrification temperature from the working temperature of the glass base material is 0° C. to 200° C., devitrification during glass formation is suppressed, and a further homogeneous glass flake is obtained.

When the glass transition temperature of the glass base material is 550° C. to 700° C., the heat resistance of the glass flake is improved.

When ΔW, which is an index for acid resistance of the glass base material, is 0.05 to 1.5 percent by mass, the acid resistance of the glass flake is increased.

In a coated glass flake formed by coating the surface of a glass flake with a coating of which a main component is metal or metal oxide, the coating colors produce a metallic color, an interference color, or the like.

EMBODIMENTS OF THE INVENTION

One embodiment will now be discussed in detail with reference to the drawings.

In this specification, a numerical value indicating a composition will be expressed as percent by mass. The composition of a glass base material for fabricating glass flakes of the present embodiment will be set as shown below, expressed in percent by mass:

$60 \leq SiO_2 \leq 75$, $5 < Al_2O_3 \leq 15$, $3 \leq CaO \leq 20$, $6 \leq Na_2O \leq 20$, and $9 \leq (Li_2O+Na_2O+K_2O) \leq 20$.

In this specification, $SiO_2$ refers to silicon dioxide (silica), $Al_2O_3$ refers to aluminum oxide (alumina), CaO refers to calcium oxide, $Li_2O$ refers to lithium oxide, $Na_2O$ refers to sodium oxide, and $K_2O$ refers to potassium oxide.

Figure 1:
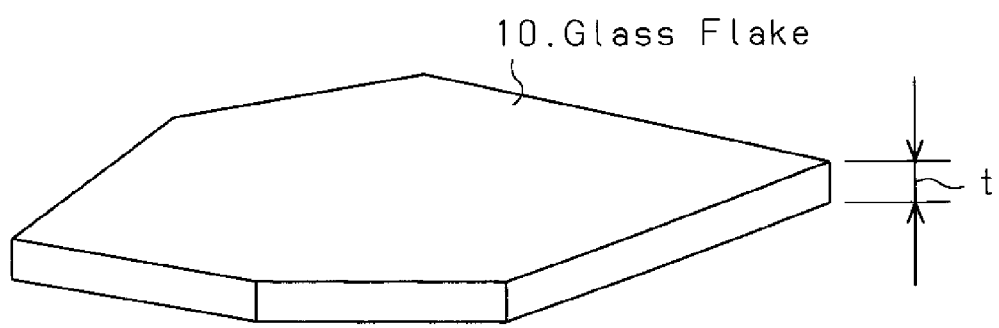
FIG. 1(a) is a schematic perspective view showing a glass flake in one embodiment.
FIG. 1(b) is a plan view showing the glass flake.
Figure 1:
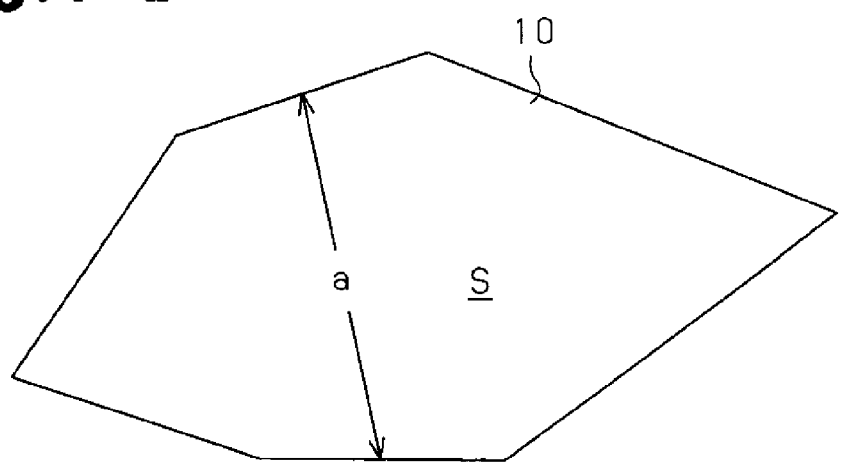

FIG. 1(a) is a perspective view showing a glass flake 10, and FIG. 1(b) is a plan view showing the glass flake 10. Referring to FIG. 1(a), the glass flake 10 of the present embodiment has an average thickness t of 0.1 to 15 μm. Further, the glass flake 10 has an aspect ratio (average grain diameter a/average thickness t) of 2 to 1000. Accordingly, the glass flake 10 is a thin grain. The glass flake 10 may have a planar shape that is hexagonal as shown in FIG. 1(b), pentagonal, octagonal, and so on. In this specification, the average grain diameter "a" is defined as the square root of the area S of the glass flake 10 when viewed from above as shown in FIG. 1(*b*), or $a=S^{1/2}$.

Next, the composition of the glass flake 10, the fabrication method of the glass flake 10, the physical properties of the glass flake 10, a coated glass flake, and applications (resin composition, paint, ink composition, and cosmetics) will be sequentially described.

Composition of Glass Flake 10

The composition of the glass base material that fabricates the glass flake 10 will now be described.

($SiO_2$)

Silicon dioxide ($SiO_2$) is a main component that forms a skeleton for the glass flake 10. In this specification, the main component refers to the component having the largest content. Further, $SiO_2$ is a component that adjusts the devitrification temperature and viscosity when forming glass while maintaining the heat resistance of the glass. When the content of $SiO_2$ is less than 60 percent by mass, the devitrification temperature rises too much. This makes it difficult to fabricate the glass flake 10 and decreases the acid resistance of the glass flake 10. When the content of $SiO_2$ exceeds 75 percent by mass, the melting point of glass becomes too high and it becomes difficult to uniformly melt the crude material.

Accordingly, the lower limit for $SiO_2$ is 60 percent by mass or greater, preferably 63 percent by mass or greater, more preferably 64 percent by mass or greater, and most preferably greater than 65 percent by mass. The upper limit for $SiO_2$ is 75 percent by mass or less, preferably 70 percent by mass or less, more preferably 68 percent by mass or less, and most preferably 67 percent by mass or less. Thus, the range for the content of $SiO_2$ is selected from any combination of these upper and lower limits and is, for example, preferably 63 to 70 percent by mass.

($B_2O_3$)

Diboron trioxide ($B_2O_3$) is a component that forms the skeleton for glass and is a component that adjusts the devitrification temperature and viscosity when forming the glass. When the content of $B_2O_3$ exceeds 6 percent by mass, this corrodes the furnace wall of a melting kiln or heat storage kiln and greatly shortens the life of the kiln. Accordingly, the upper limit of $B_2O_3$ is preferably 6 percent by mass or less, more preferably less than 2 percent by mass, and even more preferably less than 1 percent by mass. Most preferably, $B_2O_3$ is substantially not contained.

($Al_2O_3$)

Aluminum oxide ($Al_2O_3$) is a component that forms a skeleton for the glass flake 10 and is a component that adjusts the devitrification temperature and viscosity of glass when forming glass while maintaining the heat resistance. Further, $Al_2O_3$ is a component that increases the water resistance, while decreasing the acid resistance. When $Al_2O_3$ is 5 percent by mass or less, the devitrification temperature and viscosity cannot be sufficiently adjusted and/or the water resistance cannot be sufficiently improved. When the content of $Al_2O_3$ exceeds 15 percent by mass, the melting point of glass becomes too high, uniform melting of the glass becomes difficult, and the acid resistance decreases. Accordingly, the lower limit of $Al_2O_3$ is greater than 5 percent by mass, preferably 6 percent by mass or greater, more preferably 7 percent by mass or greater, and most preferably 8 percent by mass or greater. The upper limit of $Al_2O_3$ is 15 percent by mass or less, preferably 13 percent by mass or less, and most preferably less than 12 percent by mass. Thus, the range for the content of $Al_2O_3$ is selected from any combination of these upper and lower limits and is, for example, preferably 8 to 13 percent by mass.

(MgO)

Magnesium oxide (MgO) is a component that adjusts the devitrification temperature and viscosity when forming glass, while maintaining the heat resistance of glass. Although MgO is not essential, MgP may be used as a component that adjusts the devitrification temperature and viscosity when forming glass. However, when the content of MgO exceeds 10 percent by mass, the devitrification temperature rises too much, and it becomes difficult to fabricate the glass flake 10. Accordingly, the lower limit of MgO is preferably 0 percent by mass or greater, more preferably 0.1 percent by mass or greater, even more preferably 1 percent by mass or greater, and more preferably 2 percent by mass or greater. The upper limit of MgO is preferably 10 percent by mass or less, more preferably 8 percent by mass or less, even more preferably 5 percent by mass or less, and most preferably 4 percent by mass or less. Thus, the range for the content of MgO is selected from any combination of these upper and lower limits and is, for example, preferably 0.1 to 5 percent by mass.

(CaO)

Calcium Oxide (CaO) is a Component that Adjusts the devitrification temperature and viscosity when forming glass, while maintaining the heat resistance of glass. However, the content of the preferable CaO differs depending on the total content of alkali metal oxides ($Li_2O+Na_2O+K_2O$).

The content of CaO when the total content of alkali metal oxides ($Li_2O+Na_2O+K_2O$) is $9\leq(Li_2O+Na_2O+K_2O)\leq13$ will now be described. In this case, the content of CaO is set to $5\leq CaO\leq20$. When the content of CaO is less than 5 percent, the devitrification temperature and viscosity cannot be sufficiently adjusted. When the content of CaO exceeds 20 percent by mass, the devitrification temperature rises too much, and it becomes difficult to fabricate the glass flake 10. Accordingly, the lower limit of CaO is 5 percent by mass or greater, preferably 10 percent by mass or greater, more preferably 12 percent by mass or greater, and most preferably greater than 13 percent. The upper limit of CaO is 20 percent by mass or less, preferably 18 percent by mass or less, and more preferably 16 percent by mass or less. Thus, the range for the content of CaO is selected from any combination of these upper and lower limits and is, for example, preferably 10 to 18 percent by mass.

The content of CaO when the total content of alkali metal oxides ($Li_2O+Na_2O+K_2O$) is $13<(Li_2O+Na_2O+K_2O)\leq20$ will now be described. In this case, the content of CaO is set to $3\leq CaO\leq15$. When the content of CaO is less than 3 percent by mass, the devitrification temperature and viscosity cannot be sufficiently adjusted. When the content of CaO exceeds 15 percent by mass, the devitrification temperature rises too much, and it becomes difficult to fabricate the glass flake 10. Accordingly, the lower limit of CaO is 3 percent by mass or greater, preferably 4 percent by mass or greater, more preferably 5 percent by mass or greater, and most preferably 6 percent by mass or greater. The upper limit of CaO is 15 percent by mass or less, preferably 12 percent by mass or less, and more preferably 10 percent by mass or less. Thus, the range for the content of CaO is selected from any combination of these upper and lower limits and is, for example, preferably 4 to 12 percent by mass.

(SrO)

Strontium oxide (SrO) is a component that adjusts the devitrification temperature and viscosity when forming glass. SrO is also a component that decreases the acid resistance of glass. SrO is not essential but may be used as a component that adjusts the devitrification temperature and viscosity when forming glass. However, when the content of SrO exceeds 10 percent by mass, the acid resistance decreases.

Accordingly, the upper limit of SrO is preferably 10 percent by mass or less, more preferably 5 percent by mass or less, and even more preferably 2 percent by mass or less. Most preferably, SrO is substantially not contained.

(BaO)

Barium oxide (BaO) is a component that adjusts the devitrification temperature and viscosity when forming glass. BaO is also a component that decreases the acid resistance of glass. BaO is not essential but may be used as a component that adjusts the devitrification temperature and viscosity when forming glass. However, when the content of BaO exceeds 10 percent by mass, the acid resistance decreases. Accordingly, the upper limit of BaO is preferably 10 percent by mass or less, more preferably 5 percent by mass or less, and even more preferably 2 percent by mass or less. Most preferably, BaO is substantially not contained.

(ZnO)

Zinc oxide (ZnO) is a component that adjusts the devitrification temperature and viscosity when forming glass. ZnO easily evaporates and may thus scatter when it is molten. When the content of ZnO exceeds 10 percent by mass, variation in the component ratio resulting from the evaporation becomes prominent, and management of the content in glass becomes difficult. Accordingly, the upper limit of ZnO is preferably 10 percent by mass or less, more preferably 5 percent by mass or less, and even more preferably 2 percent by mass or less. Most preferably, ZnO is substantially not contained.

($Li_2O$, $Na_2O$, $K_2O$)

Alkali metal oxides ($Li_2O$, $Na_2O$, and $K_2O$) are components that adjust the devitrification temperature and viscosity when forming glass, while maintaining the heat resistance of glass. The total content of alkali metal oxides ($Li_2O+Na_2O+K_2O$) is $9 \leq (Li_2O+Na_2O+K_2O) \leq 13$ and $13 < (Li_2O+Na_2O+K_2O) \leq 20$. By increasing the content of alkali metal oxides in this manner, the devitrification temperature of glass is easily lowered, and the viscosity of glass is easily decreased. In other words, devitrification of glass may be easily suppressed, and formability of glass may be improved at the same time. Accordingly, the productivity of the glass flake 10 may be improved.

When ($Li_2O+Na_2O+K_2O$) is less than 9 percent by mass, the melting point of glass becomes too high and it becomes difficult to uniformly melt the crude material. The fabrication of the glass flake 10 also becomes difficult. When ($Li_2O+Na_2O+K_2O$) exceeds 20 percent by mass, the glass transition temperature becomes low, and the heat resistance of glass decreases. Accordingly, the lower limit of ($Li_2O+Na_2O+K_2O$) is 9 percent by mass or greater, preferably 9.5 percent by mass or greater, and more preferably 10 percent by mass or greater. The upper limit of ($Li_2O+Na_2O+K_2O$) is 20 percent by mass or less, preferably 18 percent by mass or less, more preferably 16 percent by mass or less, and most preferably less than 15 percent by mass.

Lithium oxide ($Li_2O$) is not essential but it is desirable that it be used as a component for adjusting the devitrification temperature and viscosity when forming glass. Further, since $Li_2O$ has an effect for lowering the melting point of glass, the glass crude material easily and uniformly melts when containing it. Further, $Li_2O$ has an effect for lowering the working temperature. This results in easy fabrication of the glass flake 10. However, when the content of $Li_2O$ exceeds 5 percent by mass, the glass transition temperature becomes low, and the heat resistance of glass decreases. Moreover, the working temperature becomes too low relative to the devitrification temperature, and the fabrication of the glass flake 10 becomes difficult. Accordingly, the lower limit of $Li_2O$ is preferably 0 percent by mass or greater, more preferably 0.1 percent by mass or greater, even more preferably 0.5 percent by mass or greater, and most preferably 1 percent by mass or greater. The upper limit of $Li_2O$ is preferably 5 percent by mass or less, more preferably 4 percent by mass or less, even more preferably 3 percent by mass or less, and most preferably less than 2 percent by mass. The range of $Li_2O$ is selected from any combination of these upper and lower limits and is, for example, preferably 0.1 percent by mass to 4 percent by mass or less.

Sodium oxide ($Na_2O$) is used as a component for adjusting the devitrification temperature and viscosity when forming glass. However, the preferable content of $Na_2O$ differs depending on the total content of alkali metal oxides ($Li_2O+Na_2O+K_2O$).

The content of $Na_2O$ when the total content of alkali metal oxides ($Li_2O+Na_2O+K_2O$) is $9 \leq (Li_2O+Na_2O+K_2O) \leq 13$ will now be described. In this case, when the content of $Na_2O$ is less than 6 percent by mass, the melting point of glass becomes too high, and it becomes difficult to uniformly melt the crude material. The fabrication of the glass flake 10 also becomes difficult. Accordingly, the lower limit of the content of $Na_2O$ is 6 percent by mass or greater, preferably 7 percent by mass or greater, more preferably 8 percent by mass or greater, and most preferably 9 percent by mass or greater. The upper limit of the content of $Na_2O$ is 13 percent by mass or less and preferably 12 percent by mass or less. The range of $Na_2O$ is selected from any combination of these upper and lower limits and is preferably, for example, 7 percent by mass to 12 percent by mass or less.

The content of $Na_2O$ when the total content of alkali metal oxides ($Li_2O+Na_2O+K_2O$) is $13 < (Li_2O+Na_2O+K_2O) \leq 20$ will now be described. In this case, when the content of $Na_2O$ exceeds 20 percent by mass, the glass transition temperature becomes low, and the heat resistance of glass decreases.

Accordingly, the lower limit of the content of $Na_2O$ is 9 percent by mass or greater, preferably 10 percent by mass or greater, more preferably 11 percent by mass or greater, and most preferably 12 percent by mass or greater. The upper limit of the content of $Na_2O$ is 20 percent by mass or less, preferably 17 percent by mass or less, more preferably less than 15 percent, and most preferably 14 percent by mass or less. The range of $Na_2O$ is selected from any combination of these upper and lower limits and is preferably, for example, 10 percent by mass to 17 percent by mass or less.

Potassium oxide ($K_2O$) is not essential but it is desirable that it be used as a component for adjusting the devitrification temperature and viscosity when forming glass. However, when the content of $K_2O$ exceeds 5 percent by mass, the glass transition temperature becomes low, and the heat resistance of glass decreases. Accordingly, the lower limit of $K_2O$ is preferably 0 percent by mass or greater, more preferably 0.1 percent by mass or greater, and even more preferably 0.5 percent by mass or greater. The upper limit of $K_2O$ is preferably 5 percent by mass or less, more preferably 3 percent by mass or less, even more preferably less than 2 percent by mass, and most preferably 1 percent by mass or less. The content of $K_2O$ is selected from any combination of these upper and lower limits and is, for example, 0.1 percent by mass to 3 percent by mass or less.

($TiO_2$)

Titanium oxide ($TiO_2$) is a component that increases the meltability of glass and the chemical durability and ultraviolet absorptivity of the glass flake 10. Although $TiO_2$ is not an essential component, it is thus preferable that $TiO_2$ be contained as a component that adjusts the meltability of glass and the chemical durability and optical property of the glass flake 10. However, when the content of $TiO_2$ exceeds 5 percent by mass, the devitrification temperature rises too much and fabrication of the glass flake 10 becomes difficult. Accordingly, the lower limit of $TiO_2$ is preferably 0 percent by mass or greater and more preferably 0.1 percent by mass or greater. The upper limit of $TiO_2$ is preferably 5 percent by mass or less, more preferably 2 percent by mass or less, and even more preferably less than 1 percent by mass.

($ZrO_2$)

Zirconium dioxide ($ZrO_2$) is a component that adjusts the devitrification temperature and viscosity when forming glass. Further, $ZrO_2$ functions to increase the speed of devitrification growth for glass. However, when the content of $ZrO_2$ exceeds 5 percent by mass, the devitrification temperature rises too much and fabrication of the glass flake 10 becomes difficult. Accordingly, the upper limit of $ZrO_2$ is preferably 5 percent by mass or less, more preferably 2 percent by mass or less, and even more preferably 1 percent by mass or less. It is most preferable that $ZrO_2$ be substantially not contained.

(Fe)

Iron (Fe) normally exists in glass in the state of $Fe^{2+}$ or $Fe^{3+}$. $Fe^{3+}$ is a component that increases the ultraviolet absorptivity of the glass flake 10, and $Fe^{2+}$ is a component that increases the heat-ray absorptivity. Although iron (Fe) is not an essential component, it is preferable that iron (Fe) be contained as a component that adjusts the optical property of the glass flake 10. Further, even when not intended to be contained, iron (Fe) from other industrial crude materials may become inevitably mixed therein. When the content of iron (Fe) increases, coloring of the glass flake 10 becomes prominent. Such coloring may not be preferable for applications in which the color tone and luster of the glass flake 10 are important. Accordingly, the upper limit of iron (Fe) in $Fe_2O_3$ equivalent is preferably 5 percent by mass or less, more preferably 2 percent by mass or less, even more preferably 0.5 percent by mass or less, and in particular preferably 0.1 percent by mass or less. It is most preferable that iron (Fe) be substantially not contained.

($SO_3$)

Although Sulfur Trioxide ($SO_3$) is not an Essential component, it may be contained as a fining agent. When using sulfate crude material, sulfur trioxide may be contained with a content of 0.5 percent by mass or less.

(F)

Fluorine (F) easily evaporates and may thus scatter when melting. Further, management of the content in glass is difficult. Accordingly, it is preferable that F be substantially not contained.

(MgO+CaO)

When it is significant that the glass flake 10 be easy to fabricate, the sum (MgO+CaO) of the contents is important of MgO and CaO, which are components for adjusting the devitrification temperature and viscosity when forming glass. However, the preferable sum (MgO+CaO) of the contents of MgO and CaO differs depending on the total content of alkali metal oxides ($Li_2O+Na_2O+K_2O$).

The sum (MgO+CaO) of the contents of MgO and CaO when the total content of alkali metal oxides ($Li_2O+Na_2O+K_2O$) is $9\leq(Li_2O+Na_2O+K_2O)\leq13$ will now be described. In this case, it is preferable that the sum be $5\leq(MgO+CaO)\leq30$. When (MgO+CaO) is less than 5 percent by mass, the acid resistance of the glass flake 10 becomes insufficient. When (MgO+CaO) exceeds 30 percent by mass, the devitrification temperature rises too much and fabrication of the glass flake 10 becomes difficult. Accordingly, the lower limit of (MgO+CaO) is preferably 5 percent by mass or greater, more preferably 11 percent by mass or greater, even more preferably 13 percent by mass or greater, and most preferably greater than 14 percent by mass. The upper limit of (MgO+CaO) is preferably 30 percent by mass or less, more preferably 26 percent by mass or less, even more preferably 23 percent by mass or less, and most preferably 20 percent by mass or less. The range of (MgO+CaO) is selected from any combination of these upper and lower limits and is, for example, 11 to 26 percent by mass.

The sum (MgO+CaO) of the contents of MgO and CaO when the total content of alkali metal oxides ($Li_2O+Na_2O+K_2O$) is $13<(Li_2O+Na_2O+K_2O)\leq20$ will now be described. In this case, it is preferable that the sum be $3\leq(MgO+CaO)\leq25$. When (MgO+CaO) is less than 3 percent by mass, the acid resistance of the glass flake 10 becomes insufficient. When the content of (MgO+CaO) exceeds 25 percent by mass, the devitrification temperature rises too much and fabrication of the glass flake 10 becomes difficult. Accordingly, the lower limit of (MgO+CaO) is preferably 3 percent by mass or greater, more preferably 6 percent by mass or greater, even more preferably 8 percent by mass or greater, and most preferably 10 percent by mass or greater. The upper limit of (MgO+CaO) is preferably 25 percent by mass or less, more preferably 20 percent by mass or less, even more preferably 17 percent by mass or less, and most preferably 15 percent by mass or less. The range of (MgO+CaO) is selected from any combination of these upper and lower limits and is, for example, 8 to 17 percent by mass.

In the present embodiment, when a substance is substantially not contained, this would mean that the substance is intentionally not contained although industrial crude materials, for example, may become inevitably mixed therein. More specifically, such a phrase would refer to a content that is less than 0.1 percent by mass.

As described above in detail, the glass base material for fabricating the glass flake 10 in the present embodiment contains the essential components of $SiO_2$, $Al_2O_3$, CaO, and $Na_2O$. When necessary, the glass base material may also contain $B_2O_3$, MgO, SrO, BaO, ZnO, $Li_2O$, $K_2O$, $TiO_2$, $ZrO_2$, iron oxide (FeO or $Fe_2O_3$), $SO_3$, and the like.

Process for Fabricating Glass Flake 10

Figure 4:
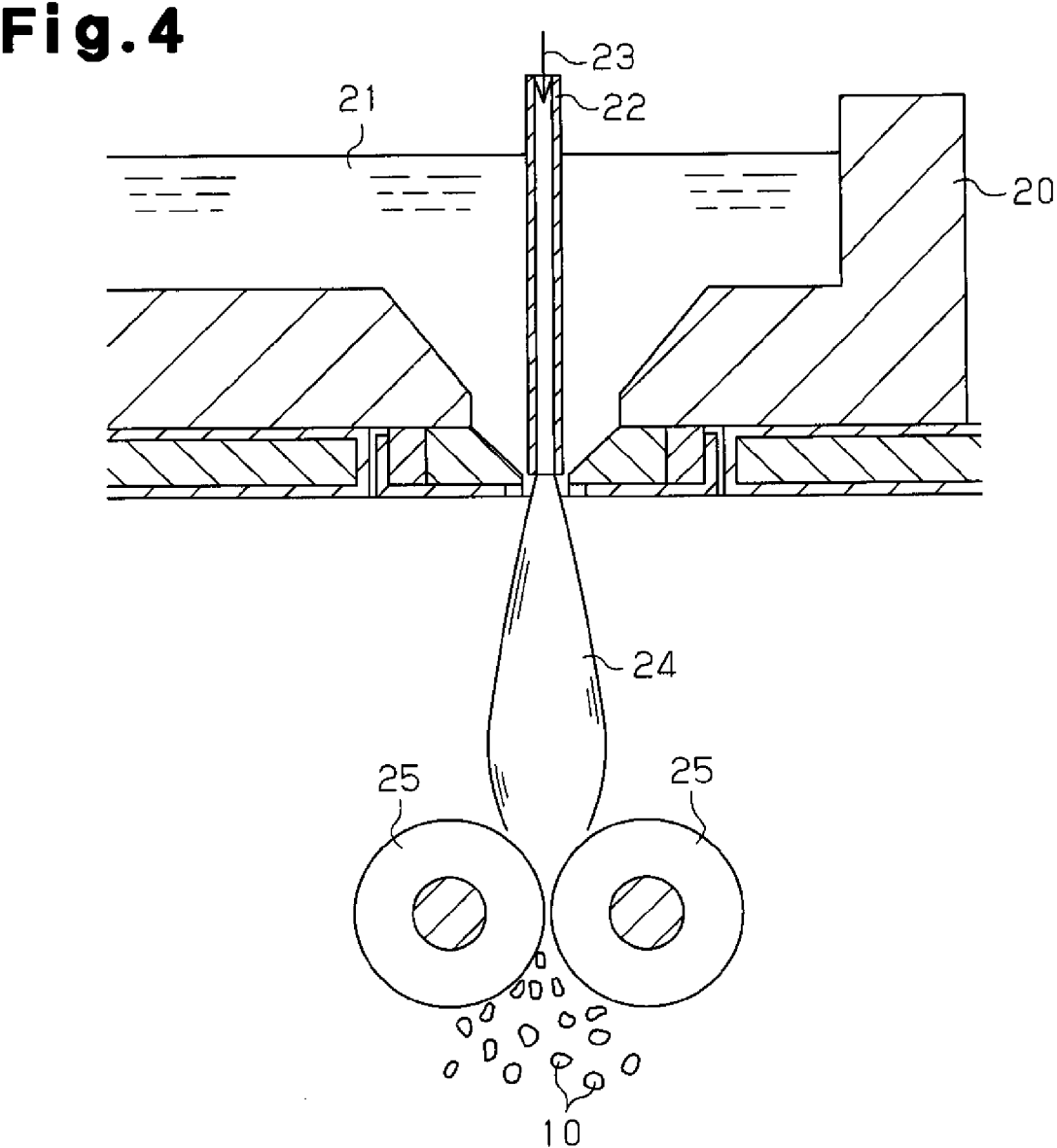
FIG. 4 is a cross-sectional view showing an apparatus for fabricating the glass flakes.

The glass flake 10 of the present embodiment may be fabricated using, for example, a fabrication apparatus that is shown in FIG. 4. Referring to FIG. 4, a glass base material 21, which is melted in a fire-retardant kiln basin and has the glass composition described above, is inflated by gas 23 delivered through a blow nozzle 22 into a balloon to form a hollow glass film 24. The resulting hollow glass film 24 is crushed by two pressing rollers 25 to obtain glass flakes 10.

Figure 5:
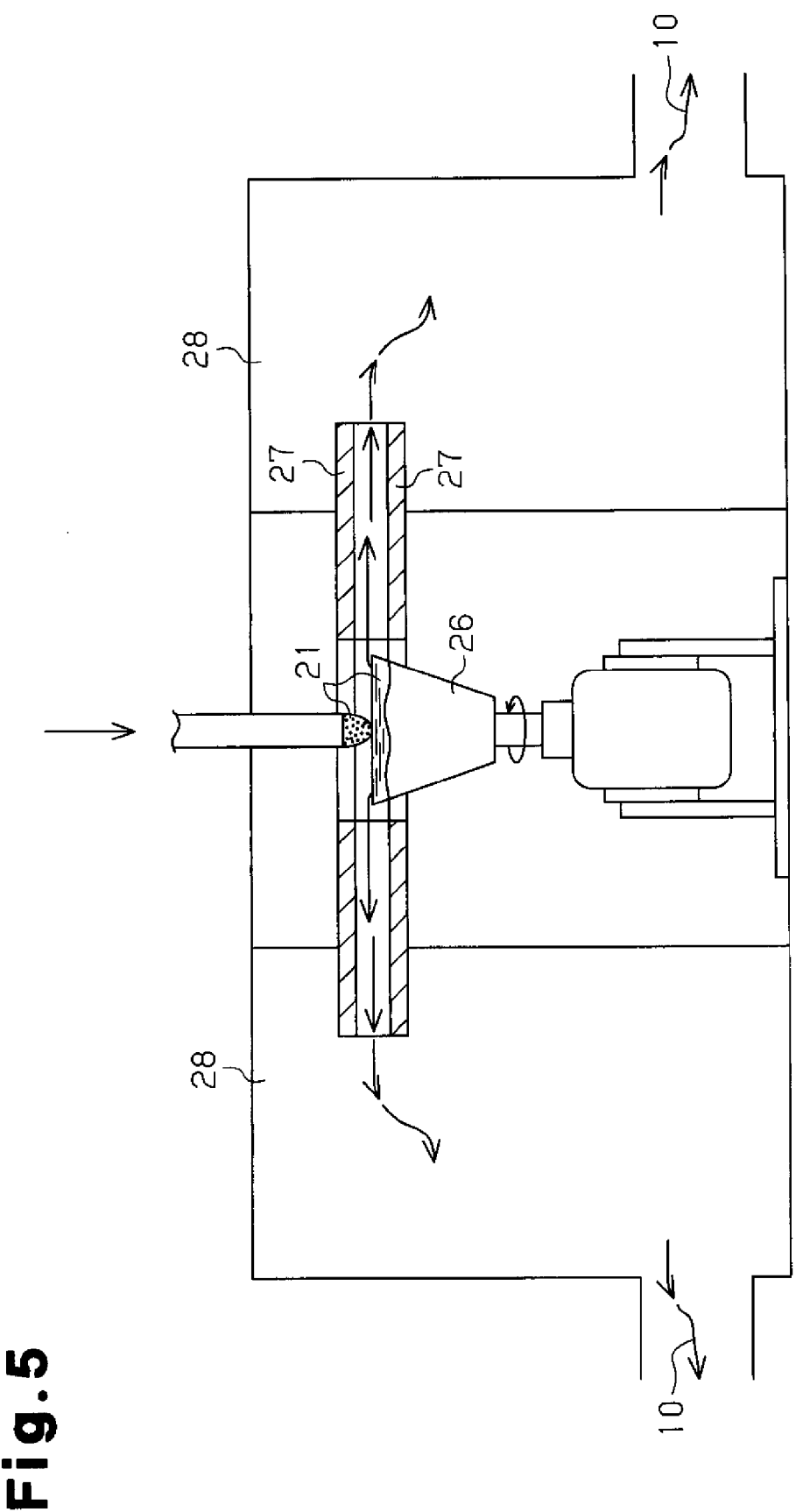
FIG. 5 is a cross-sectional view showing another apparatus for fabricating the glass flakes.

The glass flake 10 of the present embodiment may also be fabricated using, for example, a fabrication apparatus that is shown in FIG. 5. Referring to FIG. 5, a molten-state glass base material 21, which is poured into a rotary cup 26 and has the glass composition described above, is centrifugally discharged in the radial direction from the upper end of the rotary cup 26, drawn by an air flow into a gap between upper and lower annular plates 27, and sent into an annular cyclone-type collector 28. When passing through the gap between the annular plates 27, the glass base material 21 is cooled and solidified in the form of a thin film and then crushed into fine pieces to obtain glass flakes 10.

Physical Properties of Glass Composition

The physical properties of the glass flakes 10 in the present embodiment will now be discussed in detail.

(Thermal Property)

The temperature when the viscosity of molten glass is 100 Pa·sec (1000 P) is referred to as the working temperature and is most suitable for forming the glass flakes 10. For example, with the fabrication apparatus of FIG. 4, the average thickness of the hollow glass film 24, that is, the average thickness of the glass flakes 10, is preferably 0.1 to 15 µm. When forming such a thin hollow glass film 24, the temperature of the glass decreases drastically. Due to the temperature decrease, the plasticity of the hollow glass film 24 suddenly decreases and makes the hollow glass film 24 difficult to elongate. The decrease in plasticity makes it difficult for the hollow glass film 24 to grow uniformly, and variations may occur in the glass film thickness. The average thickness of the glass flakes 10 obtained in this manner is preferably 0.1 to 15 µm, more preferably 0.5 to 5 µm, and in particular preferably 0.5 to 1 µm. When the average thickness of the glass flakes 10 is less than 0.1 µm, it becomes difficult to prepare the glass flakes 10 with a high level of uniformity. When the average thickness is greater than 15 µm, the thickness of the glass flakes 10 becomes uneven.

The working temperature is 1180° C. to 1300° C. When the working temperature is less than 1180° C., it becomes difficult to uniformly form the hollow glass film 24. As a result, it becomes difficult to obtain the glass flakes 10 with a high level of uniformity. When the working temperature exceeds 1300° C., the glass fabrication apparatus is apt to being corroded by heat. This may shorten the life of the apparatus. The lower limit of the working temperature is preferably 1180° C. or greater, more preferably 1200° C. or greater, even more preferably 1210° C. or greater, and most preferably 1220° C. or greater. The upper limit of the working temperature is preferably 1300° C. or less, more preferably 1280° C. or less, even more preferably 1260° C. or less, and most preferably 1250° C. or less. Thus, it is preferable that the working temperature be, for example, 1200° C. to 1280° C.

The devitrification temperature is about 1050° C. to about 1200° C. In this specification, devitrification refers to a situation in which crystals generated and grown from the glass base material 21 become turbid. Glass fabricated from such molten glass base material 21 may include crystallized agglomerates and thus is not preferable for use as a glass flake 10.

An increase in the temperature difference ΔT, which is obtained by subtracting the devitrification temperature from the working temperature, would result in devitrification being less likely to occur during glass formation, and homogeneous glass flakes 10 may be fabricated with a high yield. For example, the fabrication apparatus shown in FIGS. 4 and 5 may be used to fabricate the glass flakes 10 with a high yield when glass having a temperature difference ΔT of 0° C. or greater is used. Accordingly, ΔT is preferably 0° C. or greater, more preferably 30° C. or greater, even more preferably 40° C. or greater, and most preferably 60° C. or greater. However, to facilitate adjustments in the glass composition, it is preferable that ΔT be 200° C. or less. It is more preferable that ΔT be 180° C. or less and particularly preferable that ΔT be 160° C. or less. Thus, the temperature difference ΔT is preferably, for example, 20° C. to 180° C.

(Glass Transition Temperature)

The glass flakes 10 have a heat resistance that increases as the glass transition temperature (glass transition point, Tg) increases and become difficult to deform when undergoing processing that requires heating to a high temperature. As long as the glass transition temperature is 550° C. or greater, the shapes of the glass flakes 10 are unlikely to change in a process for forming on the surfaces of the glass flakes 10 a coating of which main component is a metal or metal oxide. The glass flakes 10 or coated glass flakes may be blended with paint and be used for an application such as baking finishing. The glass composition specified in the present embodiment easily obtains glass having a glass transition temperature of 550° C. or greater. The glass transition temperature of the glass flakes 10 is preferably 550° C. or greater, more preferably 560° C. or greater, even more preferably 570° C. or greater, and most preferably 580° C. or greater. The upper limit of the glass transition temperature is preferably about 700° C. and more preferably 650° C. or less. Accordingly, the glass transition temperature is preferable 550° C. to 700° C. and more preferably 560° C. to 650° C.

(Chemical Durability)

The glass flakes 10 of the present embodiment have superior chemical durability, such as acid resistance, water resistance, and alkali resistance. Thus, the glass flakes 10 of the present embodiment are optimal for use in applications such as a resin mold product, paint, cosmetics, and ink.

As an index for acid resistance, a mass decrease rate ΔW measured as follows was used. The glass base material for fabricating the glass flakes 10 was crushed and passed through a supplemental mesh sieve of 710 µm and a standard mesh sieve of 590 µm, which are specified by JIS Z 8801. An amount of glass powder with a size that did not pass through a standard mesh sieve of 420 µm corresponding to the same grams as the specific gravity of glass was immersed for 72 hours in 100 mL of 10 percent by mass of a sulfuric acid aqueous solution at 80° C. to obtain the mass decrease rate ΔW. A lower mass decrease rate ΔW indicates higher acid resistance. This measurement method is in compliance with "Measurement Method (Powder Method) of Chemical Durability for Optical Glass 06-1975" of the Japan Optical Glass Industrial Standard (JOGIS). However, in the examples described later, instead of using 0.01 N (mol/L) of nitric acid aqueous solution as specified by the JOGIS measurement method, 10 percent by mass of sulfuric acid aqueous solution was used. The temperature of the sulfuric acid aqueous solution was set to 80° C., and the liquid amount was set to 100 mL instead of the 80 mL as specified in the JOGIS measurement method. Further, the processing time was 72 hours instead of 60 minutes as specified in the JOGIS measurement method. The glass base material for fabricating the glass flakes 10 is a glass sample manufactured by melting conventional glass crude materials.

When using paint or the like containing the glass flakes 10 as corrosion-resistant lining under an acid environment, it is desirable that the above-described index (mass decrease rate ΔW) indicating the acid resistance of glass be a small value. When the mass decrease rate ΔW is a large value, the corrosion resistance of the corrosion-resistant lining under an acid environment becomes low. Accordingly, the mass decrease rate ΔW is preferably 1.5 percent by mass or less, more preferably 0.8 percent by mass or less, and even more preferably 0.4 percent by mass or less. The lower limit for the mass decrease rate ΔW is normally about 0.05 percent by mass and preferably 0.1 percent by mass or greater. Thus, the mass decrease rate ΔW is, for example, preferably 0.1 to 0.4 percent by mass.

Coated Glass Flake

Figure 2:
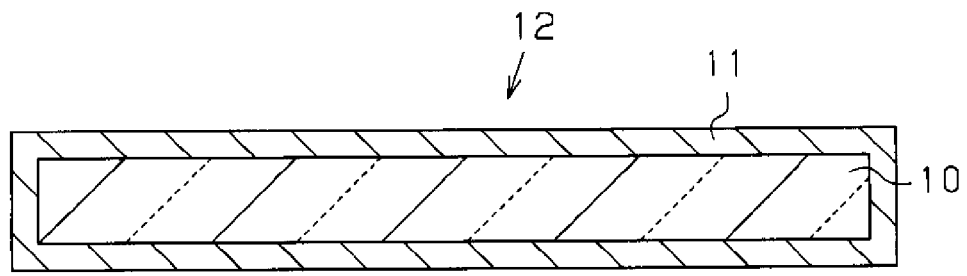
FIG. 2 is a schematic cross-sectional view showing a coated glass flake.

As schematically shown in FIG. 2, a coating 11 of which main component is metal or a metal oxide is formed on the surface of the above-described glass flake 10 as a core to fabricate a coated glass flake 12. It is preferable that the coating 11 be substantially formed by at least one of a metal and a metal oxide. The coating 11 may have any one of a single layer, mixed layer, and multiple layer structure.

More specifically, the coating 11 is formed from at least one metal selected from the group consisting of silver, gold, platinum, palladium, and nickel. Alternatively, the coating 11 is formed from at least one metal oxide selected from the group consisting of a titanium oxide, aluminum oxide, iron oxide, cobalt oxide, zirconium oxide, zinc oxide, tin oxide, and silicon dioxide. Among these substances, titanium dioxide, which has a high refractive index and transparency and in which coloring of an interference color is satisfactory, and iron oxide, which can produce a characteristic interference color, are preferable.

The coating 11 may be a laminated film including a first film, of which a main component is a metal, and a second film, of which a main component is a metal oxide.

The coating 11 may be formed on the entire surface of the glass flake 10, which serves as the core. Alternatively, the coating 11 may be formed on part of the surface of the glass flake 10.

The coating 11 may have a thickness that is set in accordance with the application. Any process such as a generally known process may be employed as a process for forming the coating 11 on the glass flake 10. For example, a known process may be employed such as a sputtering process, a sol-gel process, a chemical vapor deposition (CVD) process, a liquid phase deposition process (LPD method), or a process for depositing an oxide from a metal salt. The LPD process deposits a thin film of metal oxide on a substrate or like from a reaction solution.

Application (Resin Composition, Paint, Ink Composition, And Cosmetics)

Figure 3:
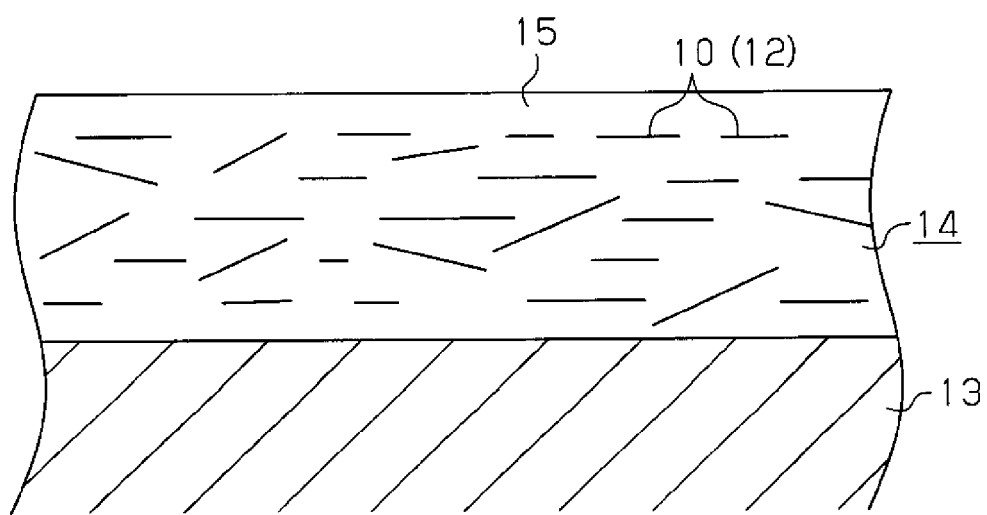
FIG. 3 is a cross-sectional view showing a state in which a coating film including glass flakes or coated glass flakes is formed on the surface of a substrate.

The glass flakes 10 or coated glass flakes 12 are blended as a pigment or reinforcement filler by a known means with a resin composition, paint, ink composition, cosmetics, and the like. This increases the color tone and lust of the resin composition, paint, ink composition, cosmetics, and the like. Further, the dimensional accuracy, strength, and the like are improved for such resin composition, paint, and ink composition. FIG. 3 is a schematic cross-sectional view showing an example of a substrate 13 having a surface coated with a paint, in which the glass flakes 10 are blended. As shown in FIG. 3, the glass flakes 10 or coated glass flakes 12 are dispersed in a resin matrix 15 of a coating film 14.

The resin composition, paint, ink composition, and cosmetics may be selected and used as required in accordance with the application as long as it is generally known. The mixture ratio of the glass flakes 10 and these materials may be set as required. Further, any method for blending the glass flakes 10 with these materials may be employed as long as it is generally known. For example, when blending the glass flakes 10 or the coated glass flakes 12 with paint, a thermosetting resin, a thermoplastic resin, or a curing agent may be selected as required and be mixed with the host material resin.

The thermosetting resin is not particularly limited and may be acrylic resin, polyester resin, epoxy resin, phenol resin, urea resin, fluorocarbon resin, polyester-urethane curable resin, epoxy-polyester curable resin, acryl-polyester resin, acryl-urethane curable resin, acryl-melamine curable resin, polyester-melamine curable resin, and the like.

The thermoplastic resin is not particularly limited and may be, for example, polyvinyl chloride, polypropylene, polyethylene, polystyrene, polyester, polyamide, polycarbonate, polybutylene, polybutylene terephthalate, a copolymer of monomers forming these substances, poly phenylene sulfide, polyphenylene ether, polyetheretherketone, liquid crystal polymer (type I, type II, or type III), thermoplastic fluorocarbon resin, or the like.

The curing agent is not particularly limited and may be polyisocyanate, amine, polyamide, polybasic acid, acid anhydride, polysulfide, boron trifluoride acid, acid dihydrazide, imidazole, or the like.

Further, when blending the glass flakes 10 or the coated glass flakes 12 in a resin composition, any of the above-described thermosetting resins or thermoplastic resins may be used as the host resin.

The ink composition may be an ink for a writing implement, such as any type of ballpoint and felt tip pens, or a printing ink, such as gravure and offset inks. The glass flakes 10 or the coated glass flakes 12 may be applied to any of such ink compositions. The vehicle forming the ink composition scatters the pigment and functions to solidify the ink on paper. The vehicle is formed from a resin, oil, and solvent.

Examples of the resin for the vehicle of a writing implement ink include an acrylic resin, a styrene-acrylic copolymer, polyvinyl alcohol, polyacrylate, acrylic monomer-vinyl acetate copolymer, a microbial polysaccharide such as xanthan gum, and a water-soluble polysaccharide such as guar gum. Further, examples of the solvent include water, alcohol, hydrocarbon, ester, and the like.

Examples of the resin for the gravure ink vehicle include gum rosin, wood rosin, tall oil rosin, lime rosin, rosin ester, a maleic resin, a polyamide resin, a vinyl resin, cellulose nitrate, cellulose acetate, ethyl cellulose, chlorinated rubber, cyclized rubber, an ethylene-vinyl acetate copolymer resin, an urethane resin, a polyester resin, an alkyd resin, gilsonite, dammar, shellac, or the like, a mixture of these resins, and a water-soluble resin or emulsion resin in which the above-described resins are dissolved. Examples of the solvent for the gravure ink vehicle include hydrocarbon, alcohol, ether, ester, and water.

Examples of the resin for the offset ink vehicle include a rosin-modified phenol resin, a petroleum resin, an alkyd resin, and a dry modified resin obtained from any one of these resins. Examples of the oil for the offset ink vehicle include vegetable oils such as linseed oil, tung oil, and soybean oil. Examples of the solvent for the offset ink vehicle include n-paraffin, isoparaffin, aromatic, naphthene, alpha-olefin, and water. Conventional additives, such as a dye, pigment, surfactant, lubricant, defoamer, and leveling agent may be selected and mixed to the vehicle components described above.

Examples of the cosmetics include a wide variety of cosmetics such as facial cosmetics, makeup cosmetics, and hair cosmetics. Among these cosmetics, application is optimal for makeup cosmetics, such as foundation, face powder, eye shadow, makeup base, nail enamel, eye liner, mascara, lipstick, and fancy powder.

In accordance with the application for cosmetics, a hydrophobizing process may be performed on the glass flakes 10 when required. The hydrophobizing process may be performed through any of the five processes described below.

(1) Process using a silicone compound such as methyl hydrogen polysiloxane, high-viscosity silicone oil or a silicone resin.

(2) Process using a surfactant such as an anion surfactant or a cationic surfactant.

(3) Process using a polymer compound such as nylon, polymethylmethacrylate, polyethylene, various types of fluorocarbon resin [polytetrafluoroethylene resin (PTFE), tetrafluoroethylene-perfluoro alkyl vinyl ether copolymer (PFA), tetrafluoroethylene-hexafluoropropylene copolymer (FEP), Tetrafluoroethylene-ethylene copolymer (ETFE), polyvinylidene fluoride (PVDF), polychlorotrifluoroethylene (PCTFE), and the like], polyamino acid.

(4) Process using a perfluoro group-containing compound, lecithin, collagen, metal soap, lipophilic wax, polyalcohol partial ester or complete ester and the like.

(5) Process combining the above processes.

Processes other than those described above may be used as long as it is applicable to a hydrophobizing process for powder.

Other materials that are commonly used for cosmetics may be blended with the above-mentioned cosmetics when required. For example, inorganic powder, organic powder, pigment or colorant, hydrocarbon, an ester, an oil component, an organic solvent, a resin, a plasticizer, an ultraviolet absorbent, an antioxidant, a preservative, a surfactant, a moisturizer, a perfume, water, alcohol, and a thickening agent may be used.

Examples of an inorganic powder include talc, kaolin, sericite, muscovite, phlogopite, lepidolite, bitotite, lithia mica, vermiculite, magnesium carbonate, calcium carbonate, diatomaceous earth, magnesium silicate, calcium silicate, aluminium silicate, barium sulfate, metal salts of tungstic acid, silica, hydroxyapatite, zeolite, boron nitride, and ceramic powder.

Examples of an organic powder include nylon powder, polyethylene powder, polystyrene powder, benzoguanamine powder, polytetrafluoroethylene powder, (distyrenebenzene polymer powder), epoxy resin powder, acrylic resin powder, and microcrystalline cellulose.

The pigment is largely classified into inorganic pigments and organic pigments.

Examples of inorganic pigments include the following as categorized in accordance with color. Inorganic white pigment: titanium oxide and zinc oxide. Inorganic red pigment: iron oxide (colcothar) and iron titanate. Inorganic brown pigments: γ-iron oxide. Inorganic yellow pigments: yellow iron oxide and yellow earth. Inorganic black pigments: black iron oxide and carbon black. Inorganic violet pigments: mango violet and cobalt violet. Inorganic green pigments: cobalt titanate. Inorganic blue pigments: such as ultramarine and Prussian blue.

Examples of pearl pigments include titanium oxide coated mica, titanium oxide coated bismuth oxychloride, bismuth oxychloride, titanium oxide coated talc, fish scale foil, and colored titanium oxide coated mica. Further, metal powder pigments include aluminum powder and copper powder.

Examples of organic pigments include red No. 201, red No. 202, red No. 204, red No. 205, red No. 220, red No. 226, red No. 228, red No. 405, orange No. 203, orange No. 204, yellow No. 205, yellow No. 401, blue No. 404, and the like.

For an extender pigment such as talc, calcium carbonate, barium sulfate, zirconium oxide, and aluminum white, the organic pigments obtained by laking the dyes described below were used. Examples of dyes includes red No. 3, red No. 104, red No. 106, red No. 227, red No. 230, red No. 401, red No. 505, orange No. 205, yellow No. 4, yellow No. 5, yellow No. 202, yellow No. 203, green No. 3, blue No. 1, and the like. Further, examples of colorants include natural colorants such as chlorophyll and β-carotene.

Examples of hydrocarbons include squalane, fluid paraffin, vaseline, micro-crystalline wax, ozokerite, ceresin, myristic acid, palmitic acid, stearic acid, oleic acid, isostearic acid, cetyl alcohol, hexyldecanol, oleyl alcohol, hexadecyl 2-ethylhexanoate, palmitic acid 2-ethylhexyl ester, 2-octyldodecyl myristate, neopentyl glycol di-2-ethylhexanoate, glycerol tris (2-ethylhexanoate), 2-octyldodecyl oleate, isopropyl myristate, glycerol triisostearate, glycerol tri(coconut oil fatty acid) ester, olive oil, avocado oil, beeswax, myristyl myristate, mink oil, and lanolin.

Further examples of the esters include silicone oil, higher fatty acids, oils and fats, and the like. Examples of the oil components include higher alcohols, wax, and the like. Examples of organic solvents include acetone, toluene, butyl acetate, and ester acetate. Examples of resins include alkyd resin, urea resin, and the like. Examples of plasticizers include camphor, acetyltributyl citrate and the like. In addition, ultraviolet absorbents, antioxidants, preservatives, surfactants, moisturizers, perfume, water, alcohol, thickening agents and the like may be used.

The form of the cosmetics is not particularly limited and may be in the form of powder, cake, pencils, sticks, paste, liquid, emulsion, cream, and the like.

The advantages of the above-discussed embodiment will now be described.

In the glass flakes 10 of the present embodiment, the composition of the glass base material for fabricating the glass flakes 10 is set to be $60 \leq SiO_2 \leq 75$ and $5 < Al_2O_3 \leq 15$. This obtains the sufficient content of silicon dioxide and aluminum oxide, and the silicon dioxide and aluminum oxide function to sufficiently form the skeleton for glass. Further, the glass transition temperature is high, the meltability is satisfactory, and the acid resistance and water resistance are increased. Moreover, the content of calcium oxide and sodium oxide is set to be $3 \leq CaO \leq 20$ and $6 \leq Na_2O \leq 20$. This adjusts the devitrification temperature and viscosity in a satisfactory manner during glass formation.

In addition, the content of lithium oxide, sodium oxide, and potassium oxide is set to be $9 \leq (Li_2O + Na_2O + K_2O) \leq 20$. In this manner, the content of alkali metal oxides is sufficient, and the devitrification temperature and viscosity are satisfactory during glass formation.

The glass flakes are fabricated from the glass base material having the composition described above. This increases the heat resistance and chemical durability of the glass flakes 10. The superior heat resistance suppresses deformation when the glass flakes 10 are heated to a high temperature. Further, due to the superior acid resistance, the glass flakes 10 may be applied to, for example, a corrosion-resistant lining under an acidic environment and is effective when used as a base material for a coating formed through liquid phase processing using an acid solution. Further, the working temperature may be controlled at a relatively low temperature. This facilitates the fabrication of the glass flakes 10.

The working temperature for the glass base material for fabricating the glass flakes 10 is set to be 1180° C. to 1300° C. This suppresses an increase in the viscosity and a decrease in the plasticity caused by a decrease in the glass temperature. This facilitates the fabrication of the glass flakes 10 having an even thickness.

The temperature difference ΔT obtained by subtracting the devitrification temperature from the working temperature for the glass base material for fabricating the glass flakes 10 is set to be 0° C. to 200° C. This suppresses devitrification when forming glass and obtains further homogeneous glass flakes 10.

The transition temperature of the glass base material for fabricating the glass flakes 10 is to be from 550° C. to 700° C. This increases the acid resistance of the glass flakes 10.

Index ΔW, which indicates the acid resistance of the glass base material for fabricating the glass flakes 10, is set at 0.05 to 1.5 percent by mass. This increases the acid resistance of the glass flakes.

In the coated glass flake 12, the surface of a glass flake 10 is coated with the coating 11, the main component of which is a metal or metal oxide. The coating 11 allows for coloring to a metallic color or interference color. Accordingly, the coated glass flakes 12 are optimal for use as a luster pigment.

The above-discussed embodiment will now be further specifically described using examples and comparative examples. However, the present invention is not limited to the examples.

EXAMPLES 1 To 60 AND COMPARATIVE EXAMPLES 1 To 4

The compositions shown in tables 1 to 7 were prepared by mixing conventional glass crude materials, such as silica sand and the like, to produce batches of glass base material for each example and comparative example. An electrical furnace was used to heat each batch to 1400° C. to 1600° C. and melt the batch. This condition was then maintained for about four hours until the composition became uniform. Then, the molten glass base material was poured onto a steel plate and slowly cooled to room temperature in the electrical furnace to obtain a glass sample.

The coefficient of thermal expansion for the glass sample prepared in this manner was measured with a commercially available dilatometer (Rigaku Corporation, Thermomechanical Analyzer TMA 8510), and the glass transition temperature was obtained from a coefficient of thermal expansion curve. The relationship between the viscosity and temperature was checked using the conventional platinum ball lifting process, and the working temperature was obtained from the results. In the platinum lifting process, first a platinum ball is immersed in molten glass. Then, to measure the viscosity, the relationship of the load (resistance) when lifting the platinum ball at a constant velocity and the gravity or buoyant force that acts on the platinum ball were applied to the Stokes's theorem, which indicates the relationship between viscosity and falling velocity when a microscopic grain settles in a fluid.

The glass sample was crushed, and the fragments of a size that passes through a standard mesh sieve of 1.0 mm, as specified by JIS Z 8801, but does not pass through a standard mesh sieve of 2.8 mm were put into a platinum boat and heated with a temperature gradient (900° C. to 1400° C.) for two hours in an electrical furnace. Then, the devitrification temperature was obtained from the maximum temperature of the electrical furnace in correspondence to the positions at which crystals appeared. To compensate for variations in the temperature behavior depending on location in the electrical furnace, the temperature behavior at a predetermined location in the electrical furnace was measured beforehand. The glass sample was arranged in the predetermined location to measure the devitrification temperature.

Tables 1 to 7 show the measurement results. The glass compositions shown in tables 1 to 7 are all values expressed in percent by mass. Here, $\Delta T$ is the temperature difference obtained by subtracting the devitrification temperature from the working temperature as described above, and $\Delta W$ is the index for acid resistance as described above. The glass sample was crushed. An amount of glass powder with a size that passed through a supplemental mesh sieve of 710 μm and a standard mesh sieve of 590 μm, which are specified by JIS Z 8801, but did not pass through a standard mesh sieve of 420 μm corresponding to the same grams as the specific gravity of glass was collected and immersed for 72 hours in 100 mL of 10 percent by mass of a sulfuric acid aqueous solution at 80° C. to obtain the mass decrease rate.

TABLE 1

| Component (mass %) or Physical Property | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| $SiO_2$ | 65.67 | 66.54 | 65.12 | 65.99 | 67.42 | 66.34 | 68.48 | 66.68 | 65.39 | 66.49 |
| $B_2O_3$ | — | — | — | — | — | 1.13 | — | — | — | — |
| $Al_2O_3$ | 8.15 | 8.13 | 9.73 | 9.72 | 8.12 | 8.11 | 8.25 | 9.82 | 9.77 | 9.79 |
| MgO | 3.52 | 3.28 | 3.26 | 3.02 | 3.04 | 3.03 | 5.76 | 4.37 | 3.74 | 3.04 |
| CaO | 8.80 | 8.20 | 8.15 | 7.55 | 7.61 | 7.59 | 4.01 | 5.80 | 9.35 | 7.61 |
| SrO | — | — | — | — | — | — | — | — | — | — |
| BaO | — | — | — | — | — | — | — | — | — | — |
| ZnO | — | — | — | — | — | — | — | — | — | — |
| $Li_2O$ | — | — | — | — | — | — | 0.50 | 0.49 | — | 0.49 |
| $Na_2O$ | 13.18 | 13.16 | 13.07 | 13.05 | 13.14 | 13.12 | 12.32 | 12.17 | 11.17 | 12.58 |
| $K_2O$ | 0.68 | 0.68 | 0.67 | 0.67 | 0.68 | 0.68 | 0.69 | 0.68 | 0.57 | — |
| $Li_2O + Na_2O + K_2O$ | 13.86 | 13.84 | 13.74 | 13.72 | 13.82 | 13.80 | 13.51 | 13.34 | 11.74 | 13.07 |
| $TiO_2$ | — | — | — | — | — | — | — | — | — | — |
| $ZrO_2$ | — | — | — | — | — | — | — | — | — | — |
| $Fe_2O_3$ | — | — | — | — | — | — | — | — | — | — |
| Glass Transisition Temperature [° C.] | 588 | 585 | 591 | 589 | 589 | 582 | 583 | 581 | 609 | 568 |
| Devitrification Temperature [° C.] | 1121 | 1106 | 1117 | 1109 | 1096 | 1082 | 1121 | 1131 | 1169 | 1104 |
| Working Temperature [° C.] | 1241 | 1251 | 1262 | 1270 | 1269 | 1244 | 1296 | 1286 | 1277 | 1265 |
| $\Delta T$ [° C.] | 120 | 145 | 145 | 161 | 173 | 162 | 175 | 155 | 108 | 161 |
| $\Delta W$ [mass %] | 0.18 | 0.17 | 0.26 | 0.25 | 0.19 | 0.22 | 0.24 | 0.24 | 0.22 | 0.23 |

TABLE 2

| Component (mass %) or Physical Property | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| $SiO_2$ | 65.64 | 66.65 | 62.84 | 63.90 | 64.79 | 65.55 | 66.63 | 67.24 | 65.96 | 65.67 |
| $B_2O_3$ | — | 1.27 | — | — | — | — | — | — | — | — |
| $Al_2O_3$ | 9.67 | 9.10 | 11.33 | 8.17 | 8.16 | 9.65 | 8.02 | 8.22 | 9.71 | 9.67 |
| MgO | 3.00 | 3.18 | 3.48 | 4.01 | 3.77 | — | — | 5.98 | 2.99 | 2.77 |

TABLE 2-continued

| Component (mass %) or Physical Property | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| CaO | 7.51 | 8.18 | 8.69 | 10.01 | 9.41 | 11.68 | 11.69 | 4.58 | 7.50 | 6.94 |
| SrO | — | — | — | — | — | — | — | — | — | — |
| BaO | — | — | — | — | — | — | — | — | — | — |
| ZnO | — | — | — | — | — | — | — | — | — | — |
| $Li_2O$ | 0.48 | 0.56 | — | — | — | 0.48 | — | — | — | — |
| $Na_2O$ | 9.98 | 10.24 | 13.00 | 13.22 | 13.20 | 11.97 | 12.99 | 13.30 | 13.04 | 12.99 |
| $K_2O$ | 3.71 | 0.82 | 0.67 | 0.68 | 0.68 | 0.67 | 0.67 | 0.68 | 0.67 | 0.67 |
| $Li_2O + Na_2O + K_2O$ | 14.17 | 11.62 | 13.67 | 13.90 | 13.88 | 13.12 | 13.66 | 13.98 | 13.71 | 13.66 |
| $TiO_2$ | — | — | — | — | — | — | — | — | 0.13 | 1.29 |
| $ZrO_2$ | — | — | — | — | — | — | — | — | — | — |
| $Fe_2O_3$ | — | — | — | — | — | — | — | — | — | — |
| Glass Transisition Temperature [° C.] | 560 | 579 | 607 | 590 | 590 | 586 | 594 | 601 | 591 | 593 |
| Devitrification Temperature [° C.] | 1114 | 1133 | 1143 | 1140 | 1129 | 1184 | 1177 | 1150 | 1120 | 1099 |
| Working Temperature [° C.] | 1275 | 1264 | 1258 | 1208 | 1223 | 1239 | 1238 | 1293 | 1275 | 1271 |
| ΔT [° C.] | 161 | 131 | 115 | 68 | 94 | 55 | 61 | 143 | 155 | 172 |
| ΔW [mass %] | 0.16 | 0.17 | 0.34 | 0.25 | 0.21 | 0.22 | 0.18 | 0.30 | 0.25 | 0.31 |

TABLE 3

| Component (mass %) or Physical Property | Ex. 21 | Ex. 22 | Ex. 23 | Ex. 24 | Ex. 25 | Ex. 26 | Ex. 27 | Ex. 28 | Ex. 29 | Ex. 30 |
|---|---|---|---|---|---|---|---|---|---|---|
| $SiO_2$ | 65.98 | 63.46 | 63.50 | 63.79 | 65.12 | 63.40 | 64.85 | 64.13 | 63.81 | 64.15 |
| $B_2O_3$ | — | — | — | — | — | — | — | — | — | — |
| $Al_2O_3$ | 9.72 | 10.92 | 10.93 | 10.98 | 11.04 | 10.91 | 10.99 | 11.04 | 10.98 | 11.04 |
| MgO | 3.02 | 3.20 | 3.01 | 3.22 | 3.24 | 2.77 | 2.33 | 3.24 | 3.12 | 3.14 |
| CaO | 7.54 | 10.84 | 12.95 | 10.89 | 10.95 | 12.33 | 11.23 | 10.95 | 11.95 | 12.02 |
| SrO | — | — | — | — | — | — | — | — | — | — |
| BaO | — | — | — | — | — | — | — | — | — | — |
| ZnO | — | — | — | — | — | — | — | — | — | — |
| $Li_2O$ | — | 0.55 | 0.46 | 1.05 | 1.49 | 0.51 | 1.54 | 1.54 | 1.00 | 1.49 |
| $Na_2O$ | 13.05 | 10.21 | 8.48 | 9.25 | 7.40 | 9.33 | 8.25 | 8.28 | 8.38 | 7.40 |
| $K_2O$ | 0.67 | 0.81 | 0.68 | 0.82 | 0.76 | 0.75 | 0.82 | 0.82 | 0.76 | 0.76 |
| $Li_2O + Na_2O + K_2O$ | 13.72 | 11.57 | 9.62 | 11.12 | 9.65 | 10.59 | 10.61 | 10.64 | 10.14 | 9.65 |
| $TiO_2$ | — | — | — | — | — | — | — | — | — | — |
| $ZrO_2$ | — | — | — | — | — | — | — | — | — | — |
| $Fe_2O_3$ | 0.03 | — | — | — | — | — | — | — | — | — |
| Glass Transisition Temperature [° C.] | 590 | 582 | 614 | 577 | 574 | 603 | 562 | 572 | 587 | 574 |
| Devitrification Temperature [° C.] | 1124 | 1169 | 1205 | 1164 | 1170 | 1198 | 1154 | 1164 | 1176 | 1178 |
| Working Temperature [° C.] | 1275 | 1240 | 1247 | 1226 | 1240 | 1241 | 1231 | 1217 | 1233 | 1225 |
| ΔT [° C.] | 151 | 71 | 42 | 62 | 70 | 43 | 77 | 53 | 57 | 47 |
| ΔW [mass %] | 0.24 | 0.30 | 0.31 | 0.26 | 0.18 | 0.31 | 0.19 | 0.23 | 0.27 | 0.23 |

TABLE 4

| Component (mass %) or Physical Property | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|
| $SiO_2$ | 64.39 | 65.71 | 65.15 | 65.31 | 63.25 | 66.78 | 65.90 | 63.56 | 63.15 | 63.20 |
| $B_2O_3$ | — | — | — | — | — | — | 0.57 | — | — | — |
| $Al_2O_3$ | 11.08 | 7.75 | 9.36 | 10.91 | 10.89 | 10.99 | 11.00 | 10.11 | 10.87 | 10.88 |
| MgO | 2.92 | 4.40 | 4.13 | 2.97 | 3.84 | 2.53 | 2.76 | 2.78 | 2.76 | 2.76 |
| CaO | 11.46 | 11.33 | 10.63 | 10.23 | 9.89 | 9.11 | 9.72 | 12.36 | 11.83 | 12.11 |
| SrO | — | — | — | — | — | — | — | — | 0.84 | — |
| BaO | — | — | — | — | — | — | — | — | — | 0.50 |
| ZnO | — | — | — | — | — | — | — | — | — | — |
| $Li_2O$ | 2.04 | 0.52 | 0.51 | 0.51 | — | 1.54 | 1.54 | 0.51 | 0.50 | 0.50 |
| $Na_2O$ | 7.29 | 9.53 | 9.45 | 9.33 | 11.32 | 8.24 | 8.25 | 9.36 | 9.30 | 9.30 |
| $K_2O$ | 0.82 | 0.77 | 0.76 | 0.75 | 0.81 | 0.82 | 0.82 | 0.75 | 0.75 | 0.75 |

TABLE 4-continued

| Component (mass %) or Physical Property | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|
| $Li_2O + Na_2O + K_2O$ | 10.15 | 10.82 | 10.72 | 10.59 | 12.13 | 10.60 | 10.61 | 10.62 | 10.55 | 10.55 |
| $TiO_2$ | — | — | — | — | — | — | — | — | — | — |
| $ZrO_2$ | — | — | — | — | — | — | — | — | — | — |
| $Fe_2O_3$ | — | — | — | — | — | — | — | — | — | — |
| Glass Transisition Temperature [° C.] | 553 | 593 | 598 | 599 | 614 | 561 | 562 | 598 | 601 | 602 |
| Devitrification Temperature [° C.] | 1147 | 1185 | 1192 | 1170 | 1175 | 1134 | 1145 | 1186 | 1185 | 1189 |
| Working Temperature [° C.] | 1204 | 1227 | 1251 | 1281 | 1263 | 1272 | 1256 | 1227 | 1242 | 1241 |
| ΔT [° C.] | 57 | 42 | 59 | 111 | 88 | 138 | 111 | 41 | 57 | 52 |
| ΔW [mass %] | 0.33 | 0.12 | 0.17 | 0.21 | 0.35 | 0.13 | 0.15 | 0.29 | 0.32 | 0.31 |

TABLE 5

| Component (mass %) or Physical Property | Ex. 41 | Ex. 42 | Ex. 43 | Ex. 44 | Ex. 45 | Ex. 46 | Ex. 47 | Ex. 48 | Ex. 49 | Ex. 50 |
|---|---|---|---|---|---|---|---|---|---|---|
| $SiO_2$ | 63.26 | 63.34 | 63.11 | 63.25 | 63.38 | 63.29 | 63.33 | 65.12 | 65.84 | 66.02 |
| $B_2O_3$ | — | — | — | — | — | — | — | 0.57 | 0.57 | 1.15 |
| $Al_2O_3$ | 10.89 | 10.90 | 10.86 | 10.89 | 10.91 | 10.89 | 10.90 | 8.14 | 7.33 | 6.51 |
| MgO | 2.77 | 2.74 | 2.60 | 2.73 | 2.77 | 2.75 | 2.74 | 3.52 | 3.53 | 3.54 |
| CaO | 11.85 | 12.18 | 11.59 | 12.17 | 12.32 | 12.24 | 12.17 | 8.80 | 8.83 | 8.85 |
| SrO | — | — | — | — | — | — | — | — | — | — |
| BaO | — | — | — | — | — | — | — | — | — | — |
| ZnO | 0.66 | — | — | — | — | — | — | — | — | — |
| $Li_2O$ | 0.50 | 0.50 | 0.50 | 0.50 | 0.51 | 0.50 | 0.50 | — | — | — |
| $Na_2O$ | 9.32 | 9.33 | 9.29 | 9.31 | 9.33 | 9.32 | 9.32 | 13.17 | 13.22 | 13.25 |
| $K_2O$ | 0.75 | 0.75 | 0.75 | 0.75 | 0.75 | 0.75 | 0.75 | 0.68 | 0.68 | 0.68 |
| $Li_2O + Na_2O + K_2O$ | 10.57 | 10.58 | 10.54 | 10.56 | 10.59 | 10.57 | 10.57 | 13.85 | 13.90 | 13.93 |
| $TiO_2$ | — | 0.26 | 1.29 | — | — | — | 0.26 | — | — | — |
| $ZrO_2$ | — | — | — | 0.40 | — | — | — | — | — | — |
| $Fe_2O_3$ | — | — | — | — | 0.03 | 0.26 | 0.03 | — | — | — |
| Glass Transisition Temperature [° C.] | 601 | 603 | 605 | 605 | 603 | 608 | 603 | 587 | 583 | 579 |
| Devitrification Temperature [° C.] | 1187 | 1188 | 1178 | 1190 | 1193 | 1189 | 1192 | 1111 | 1103 | 1086 |
| Working Temperature [° C.] | 1245 | 1241 | 1240 | 1247 | 1241 | 1240 | 1240 | 1226 | 1220 | 1203 |
| ΔT [° C.] | 58 | 53 | 62 | 57 | 48 | 51 | 48 | 115 | 117 | 117 |
| ΔW [mass %] | 0.25 | 0.31 | 0.35 | 0.29 | 0.30 | 0.24 | 0.31 | 0.21 | 0.17 | 0.16 |

TABLE 6

| Component (mass %) or Physical Property | Ex. 51 | Ex. 52 | Ex. 53 | Ex. 54 | Ex. 55 | Ex. 56 | Ex. 57 | Ex. 58 | Ex. 59 | Ex. 60 |
|---|---|---|---|---|---|---|---|---|---|---|
| $SiO_2$ | 65.41 | 65.16 | 65.46 | 65.15 | 65.53 | 65.40 | 65.51 | 65.94 | 63.56 | 66.53 |
| $B_2O_3$ | — | — | — | — | — | — | — | — | — | — |
| $Al_2O_3$ | 8.11 | 8.08 | 8.12 | 8.08 | 8.13 | 8.11 | 8.13 | 9.71 | 10.94 | 9.65 |
| MgO | 3.51 | 3.50 | 3.51 | 3.50 | 3.52 | 3.51 | 3.47 | 2.99 | 2.78 | — |
| CaO | 8.31 | 7.83 | 8.59 | 8.28 | 8.33 | 7.85 | 8.66 | 7.49 | 12.36 | 11.67 |
| SrO | 0.84 | 1.68 | — | — | — | — | — | — | — | — |
| BaO | — | — | 0.50 | 1.25 | — | — | — | — | — | — |
| ZnO | — | — | — | — | 0.66 | 1.33 | — | — | — | — |
| $Li_2O$ | — | — | — | — | — | — | — | — | 0.51 | 0.45 |
| $Na_2O$ | 13.13 | 13.08 | 13.14 | 13.08 | 13.15 | 13.13 | 13.15 | 13.04 | 9.85 | 11.08 |
| $K_2O$ | 0.68 | 0.67 | 0.68 | 0.67 | 0.68 | 0.68 | 0.68 | 0.67 | — | 0.62 |
| $Li_2O + Na_2O + K_2O$ | 13.81 | 13.75 | 13.82 | 13.75 | 13.83 | 13.81 | 13.83 | 13.71 | 10.36 | 12.15 |
| $TiO_2$ | — | — | — | — | — | — | — | 0.13 | — | — |
| $ZrO_2$ | — | — | — | — | — | — | — | 0.40 | — | — |
| $Fe_2O_3$ | — | — | — | — | — | — | — | — | 0.03 | — |
| Glass Transisition Temperature [° C.] | 586 | 584 | 586 | 585 | 586 | 585 | 589 | 591 | 575 | 592 |
| Devitrification | 1110 | 1086 | 1114 | 1105 | 1107 | 1103 | 1115 | 1110 | 1168 | 1205 |

TABLE 6-continued

| Component (mass %) or Physical Property | Ex. 51 | Ex. 52 | Ex. 53 | Ex. 54 | Ex. 55 | Ex. 56 | Ex. 57 | Ex. 58 | Ex. 59 | Ex. 60 |
|---|---|---|---|---|---|---|---|---|---|---|
| Temperature [° C.] Working Temperature [° C.] | 1237 | 1237 | 1237 | 1236 | 1240 | 1242 | 1242 | 1274 | 1243 | 1263 |
| ΔT [° C.] | 127 | 151 | 123 | 131 | 133 | 139 | 127 | 164 | 75 | 58 |
| ΔW [mass %] | 0.21 | 0.25 | 0.19 | 0.20 | 0.15 | 0.13 | 0.17 | 0.24 | 0.20 | 0.19 |

TABLE 7

| Component (mass %) or Physical Property | Com. Ex. 1 | Com. Ex. 2 | Com. Ex. 3 | Com. Ex. 4 |
|---|---|---|---|---|
| $SiO_2$ | 72.76 | 67.05 | 54.84 | 67.78 |
| $B_2O_3$ | — | 4.68 | 5.95 | — |
| $Al_2O_3$ | 1.88 | 4.02 | 14.52 | 9.98 |
| MgO | 3.58 | 2.58 | 0.38 | 8.68 |
| CaO | 7.62 | 6.53 | 22.80 | — |
| ZnO | — | 3.61 | — | — |
| $Li_2O$ | — | 0.59 | — | 0.50 |
| $Na_2O$ | 13.20 | 10.17 | 0.49 | 12.37 |
| $K_2O$ | 0.95 | 0.77 | 0.30 | 0.69 |
| $Li_2O + Na_2O + K_2O$ | 14.15 | 11.53 | 0.79 | 13.56 |
| $Fe_2O_3$ | — | — | 0.25 | — |
| F | — | — | 0.48 | — |
| Glass Transisition Temperature [° C.] | 553 | 549 | 681 | 618 |
| Devitrification Temperature [° C.] | 1020 | 986 | 1090 | 1286 |
| Working Temperature [° C.] | 1172 | 1165 | 1205 | 1331 |
| ΔT [° C.] | 152 | 179 | 115 | 45 |
| ΔW [mass %] | 0.40 | 0.50 | 7.40 | 0.56 |

The transition temperatures of examples 1 to 60 were 554° C. to 614° C. This shows that these glasses have superior heat resistance capacities. The working temperatures of these glasses were 1203° C. to 1296° C. Such temperatures allow for satisfactory viscosity and plasticity to be maintained when fabricating the glass flakes 10. Further, ΔT (working temperature—devitrification temperature) was 41° C. to 175° C. This is a temperature difference that does not cause devitrification in the fabrication process of the glass flakes 10. In these glasses, the mass decrease rate £W, which is the index of acid resistance, was 0.12 to 0.35 percent by mass. This shows that the glass flakes 10 have satisfactory acid resistance.

In contrast, the sheet glass compositions and C glasses of the prior art shown in comparative examples 1 and 2 had an $Al_2O_3$ content that was outside the range of the present invention. Thus, the glass transition temperature was 549° C. to 553° C. and lower than examples 1 to 60. Further, the working temperature was 1165° C. to 1172° C. and lower than examples 1 to 60. The E glass of the prior art shown in comparative example 3 had $SiO_2$ and CaO contents that were outside the range of the present invention. Thus, the mass decrease rate ΔW was 7.40 percent by mass, and the acid resistance was inferior to examples 1 to 60. Further, comparative example 4 did not include CaO, which is an essential component of the present invention. Thus, the working temperature was 1331° C. and higher than examples 1 to 60.

In the above results, as in examples 1 to 60, the glasses in which the contents of silicon dioxide ($SiO_2$), aluminum oxide ($Al_2O_3$), calcium oxide (CaO), and alkali metal oxides ($Li_2O$, $Na_2O$, $K_2O$) are within the range of the present invention have superior heat resistance, chemical durability (acid resistance), and formability. Moreover, the working temperature of the glass is set within the range of the present invention. This suppresses viscosity increase and plasticity decrease that would be caused by reduction in the glass temperature, and the glass flakes 10 were formed with an even thickness as described below.

Then, the glasses of examples 1 to 60 and comparative example 10 were used to fabricate the glass flakes 10 and the coated glass flakes 12. The glasses of each composition were melted again in the electrical furnace and then formed into pellets as they cooled. The pellets were fed to the fabrication apparatus shown in FIG. 4 to fabricate the glass flakes 10 homogeneously with an average thickness of 0.5 to 1 μm. An electronic microscope (Keyence Corporation, Real Surface View Microscope, VE-7800) was used to measure the thickness of glass flakes from cross-sections of 100 glass flakes and obtain the average thickness of the glass flakes.

EXAMPLES 61 To 120

Using the glass flakes having the compositions of examples 1 to 60 fabricated in this manner, the coated glass flakes 12 of examples 61 to 120 were fabricated through the procedures described below. First, the glass flakes were crushed into suitable grain diameters. Then, liquid phase processing was performed to cover the surface of the glass flakes with titanium dioxide. The liquid phase processing deposits titanium dioxide from metal salts onto the surface of the glass flakes 10. More specifically, stannous chloride dihydrate serving as a metal salt was dissolved in ion-exchanged water and diluted hydrochloric acid was added for adjustment to pH 2.0 to 2.5. The glass flakes 10 were added to the solution while being agitated and then filtered after ten minutes. Subsequently, chloroplatinic acid hexahydrate was dissolved in the ion exchanged water and the filtered glass flakes 10 were added while being agitated and filtered after ten minutes. Then, a hydrochloric acid solution (35 mass by percent) was added to the ion exchanged water to obtain a hydrochloric acid solution having pH 0.7. The glass flakes 10 were added to the acid solution while being agitated, and the solution temperature was heated to 75° C.

Further, titanium tetrachloride ($TiCl_4$) solution was added to the above solution at a rate of 0.2 g/min in titanium equivalent. At the same time, sodium hydroxide was added so as not to change the pH. Through a neutralization reaction, titanium dioxide ($TiO_2$) or its hydrate was deposited on the surface of the glass flakes 10 for two hours. Then, the glass flakes 10 on which the coatings 11 were formed were filtered and dried for two hours at 180° C. The coated glass flakes 12 fabricated in this manner were observed with an electronic microscope, and the formation of the coatings 11 of titanium oxide on the surfaces of the glass flakes 10 was confirmed.

EXAMPLES 121 To 180

Using the glass flakes having the compositions of examples 1 to 60, the coated glass flakes 12 of examples 121 to 180 were fabricated through the procedures described below. First, the glass flakes were crushed into suitable grain diameters. Then, the surfaces of the glass flakes were coated with silver by performing conventional electroless plating. The conventional electroless plating will now be described. First, preprocessing using stannous chloride and chloroplatinic acid hexahydrate were performed in the same manner as in examples 65 to 128 on the glass flakes 10. Then, 200 g of silver nitrate and a suitable amount of ammonia water were added to 10 L of ion exchanged water to prepare a silver liquid. Then, 1 kg of glass flakes that have undergone the preprocessing were added to the silver liquid while being agitated. Further, 14 percent by mass of sodium-potassium tartrate solution was added as a reduction liquid, and the surfaces of the glass flakes 10 were coated with silver. Afterwards, the glass flakes 10 were filtered and dried for two hours at 400° C. to obtain the glass flakes 10 of which surfaces had coatings 11 of silver.

The coated glass flakes 12 fabricated in this manner were observed with an electronic microscope, and the formation of the coatings 11 of silver on the surfaces of the glass flakes 10 was confirmed.

EXAMPLES 181 To 240 And COMPARATIVE EXAMPLE 12

The glass flakes 10 having the compositions of examples 1 to 60 were crushed to predetermined grain diameters and then mixed with a polyester resin to obtain the polyester resin compositions of examples 181 to 240 containing the glass flakes 10. The polyester resin compositions had satisfactory dispersibility in the glass flakes 10 and achieved a satisfactory outer appearance.

EXAMPLES 241 To 300

The coated glass flakes 12 of examples 61 to 120 were mixed with epoxy acrylate to obtain the vinyl ester paints of examples 241 to 300 containing the coated glass flakes 12. The vinyl ester paints had satisfactory dispersibility in the glass flakes 10 and achieved a satisfactory outer appearance.

EXAMPLES 301 To 360

The coated glass flakes 12 of examples 61 to 120 were mixed with a foundation, which is a facial cosmetic, to obtain the cosmetics of examples 301 to 360 containing the coated glass flakes 12. The cosmetics had satisfactory dispersibility in the coated glass flakes 12, which was satisfactory for cosmetics.

EXAMPLES 361 To 420

The coated glass flakes 12 of examples 61 to 120 were mixed with ink compositions, in which a coloring agent, a resin, and an organic solvent were mixed in predetermined amounts, to obtain the ink compositions of examples 361 to 420 containing the coated glass flakes 12. The ink compositions had satisfactory dispersibility in the glass flakes 10, which was satisfactory as ink compositions.

The above-discussed embodiment may be modified as described below.

The range of the melting temperature for the glass base material may be specified so that the average thickness of the glass flakes 10 becomes fixed.

As the alkali metal oxides ($Li_2O+Na_2O+K_2O$), cesium oxide ($Ce_2O$), rubidium oxide ($Rb_2O$), and the like, which are oxides of univalent alkali metals may be added.

As the composition of the glass base material for fabricating the glass flakes 10, among the alkali metal oxides $Li_2O$, $Na_2O$, and $K_2O$, the ranges of two components or one component may be specified to clarify the range for the components modifying the glass skeleton.

The glass flake 10 may have a cross-sectional shape in the thicknesswise direction having two parallel principal surfaces. Alternatively, the two principal surfaces may be inclined to one another (tapered).

Technical features that can be recognized from the above-discussed embodiment will now be described.

The working temperature of the glass base material is 1230° C. to 1290° C. In this case, the evenness in the thickness of the glass flakes is improved.

The average thickness of the glass flakes 10 is 0.1 to 15 µm. In this case, the evenness in the thickness of the glass flakes is increased so that the properties of the glass flakes may be used effectively.

The glass base material is set to satisfy $64 \leq SiO_2 \leq 70$. In this case, the heat resistance of the glass flakes is increased, the devitrification temperature and viscosity is satisfactory when forming glass, and the acid resistance is improved.

The metal that is the main component in the coating of the coated glass flake is at least one selected from the group consisting of nickel, gold, silver, platinum, and palladium.

The metal oxide that is the main component in the coating of the coated glass flake is at least one selected from the group consisting of titanium oxide, iron oxide, cobalt oxide, zirconium oxide, zinc oxide, tin oxide, and silicon oxide.

A resin composition being characterized by containing the glass flakes or the coated glass flakes. Such a resin composition obtains a resin molded product having improved physical properties such as strength, dimensional accuracy, and the like.

A paint being characterized by containing the glass flakes or the coated glass flakes. This adds a metallic color or luster to a paint film formed from the paint.

An ink composition being characterized by containing the glass flakes or the coated glass flakes. This adds a metallic color or luster to characters, graphics, and the like formed from the ink composition.

Cosmetics being characterized by containing the glass flakes or the coated glass flakes. This adds a color tone or luster after the cosmetics is applied to the face or the like.

The invention claimed is:

1. A glass flake being characterized in that the glass flake is formed from a glass base material having a composition expressed in percent by mass of:

$60 \leq SiO_2 \leq 75$;

$10.11 \leq Al_2O_3 \leq 15$;

$5 \leq CaO \leq 20$;

$6 \leq Na_2O \leq 13$; and $9 \leq (Li_2O+Na_2O+K_2O) \leq 13$, wherein the content of $Fe_2O_3$ is 0.5 percent by mass or less, and the content of ZnO is 2 percent mass or less, a temperature difference ΔT obtained by subtracting a devitrification temperature from a working temperature of the glass base material is 0° C. to 200° C. to suppress devitrification during glass formation, and wherein the glass flake is homogeneous and free from crystallized agglomerates.

2. The glass flake according to claim 1, wherein a working temperature for glass, which is the temperature when the viscosity of molten glass is 100 Pa·sec (1000P), is 1180° C. to 1300° C.

3. The glass flake according to claim 1, wherein the working temperature of the glass base material, is the temperature when the viscosity of molten glass is 100 Pa·sec (1000P).

4. The glass flake according to claim 1, wherein a glass transition temperature of the glass base material is 550° C. to 700° C.

5. The glass flake according to claim 1, wherein $\Delta W$, which is a mass decrease rate measured by immersing the glass base material in a sulfuric acid aqueous solution for 72 hours at 80° C. and representing an index for acid resistance of the glass base material, is 0.05 to 1.5 percent by mass.

6. A coated glass flake according to claim 1 further comprising:
a coating that covers a surface of the glass flake, the coating having a main component of metal or metal oxide.

7. The coated glass flake according to claim 6, being characterized in that the coating produces a metallic color or an interference color.

8. A method for fabricating the glass flake according to claim 1, the method comprising:
melting and then crushing a glass base material of which composition, as expressed in percent by mass, is:

$60 \leq SiO_2 \leq 75$;

$10.11 \leq Al_2O_3 \leq 15$;

$5 \leq CaO \leq 20$;

$6 \leq Na_2O \leq 13$; and $9 \leq (Li_2O+Na_2O+K_2O) \leq 13$, wherein the content of $Fe_2O_3$ is 0.5 percent by mass or less, and the content of ZnO is 2 percent mass or less, a temperature difference $\Delta T$ obtained by subtracting a devitrification temperature from a working temperature of the glass base material is 0° C. to 200° C. to suppress devitrification during glass formation, and wherein the glass flake is homogeneous and free from crystallized agglomerates.

9. A glass base material for forming the glass flake according to claim 1, wherein the glass base material has a composition as expressed in percent by mass of:

$60 \leq SiO_2 \leq 75$;

$10.11 \leq Al_2O_3 < 15$;

$5 \leq CaO \leq 20$;

$6 \leq Na_2O \leq 13$; and $9 \leq (Li_2O+Na_2O+K_2O) \leq 13$, wherein the content of $Fe_2O_3$ is 0.5 percent by mass or less, and the content of ZnO is 2 percent mass or less, a temperature difference $\Delta T$ obtained by subtracting a devitrification temperature from a working temperature of the glass base material is 0° C. to 200° C. to suppress devitrification during glass formation, and wherein the glass flake is homogeneous and free from crystallized agglomerates.

10. The glass flake according to claim 1, being characterized in that the glass flake is for a coated glass flake that produces a metallic color or an interference color.

11. A glass flake being characterized in that the glass flake is formed from a glass base material having a composition expressed in percent by mass of:

$60 \leq SiO_2 \leq 68$;

$11.33 \leq Al_2O_3 \leq 15$;

$3 \leq CaO \leq 15$;

$9 \leq Na_2O \leq 20$; and $13 < (Li_2O+Na_2O+K_2O) \leq 20$, wherein the content of $Fe_2O_3$ is 0.5 percent by mass or less, and the content of ZnO is 2 percent mass or less, a temperature difference $\Delta T$ obtained by subtracting a devitrification temperature from a working temperature of the glass base material is 0° C. to 200° C. to suppress devitrification during glass formation, and wherein the glass flake is homogeneous and free from crystallized agglomerates.

12. A method for fabricating the glass flake according to claim 11, the method comprising:
melting and then crushing a glass base material of which composition, as expressed in percent by mass, is:

$60 \leq SiO_2 \leq 68$;

$11.33 \leq Al_2O_3 \leq 15$;

$3 \leq CaO \leq 15$;

$9 \leq Na_2O \leq 20$; and $13 < (Li_2O+Na_2O+K_2O) \leq 20$, wherein the content of $Fe_2O_3$ is 0.5 percent by mass or less, and the content of ZnO is 2 percent mass or less, a temperature difference $\Delta T$ obtained by subtracting a devitrification temperature from a working temperature of the glass base material is 0° C. to 200° C. to suppress devitrification during glass formation, and wherein the glass flake is homogeneous and free from crystallized agglomerates.

13. A glass base material for forming the glass flake according to claim 11, wherein the glass base material has a composition as expressed in percent by mass of:

$60 \leq SiO_2 \leq 68$;

$11.33 \leq Al_2O_3 \leq 15$;

$3 \leq CaO \leq 15$;

$9 \leq Na_2O \leq 20$; and $13 < (Li_2O+Na_2O+K_2O) \leq 20$, wherein the content of $Fe_2O_3$ is 0.5 percent by mass or less, and the content of ZnO is 2 percent mass or less, a temperature difference $\Delta T$ obtained by subtracting a devitrification temperature from a working temperature of the glass base material is 0° C. to 200° C. to suppress devitrification during glass formation, and wherein the glass flake is homogeneous and free from crystallized agglomerates.

14. A coated glass flake comprising:
the glass flake according to claim 11; and
a coating that covers a surface of the glass flake, the coating having a main component of metal or metal oxide.

15. A glass flake is formed from a glass base material having a composition expressed in percent by mass comprising:

$63 \leq SiO_2 \leq 75$;

$10.11 \leq Al_2O_3 \leq 15$;

$5 \leq CaO \leq 20$;

$6 \leq Na_2O \leq 13$; and $9 \leq (Li_2O+Na_2O+K_2O) \leq 13$, wherein the content of $Fe_2O_3$ is 0.5 percent by mass or less, and the content of ZnO is 2 percent mass or less, a temperature difference ΔT obtained by subtracting a devitrification temperature from a working temperature of the glass base material is 0° C. to 200° C. to suppress devitrification during glass formation, and wherein the glass flake is homogeneous and free from crystallized agglomerates.

16. A glass flake is formed from a glass base material having a composition expressed in percent by mass comprising:

$63 \leq SiO_2 \leq 68$;

$11.33 \leq Al_2O_3 \leq 15$;

$3 \leq CaO \leq 15$;

$9 \leq Na_2O \leq 20$; and $13 < (Li_2O+Na_2O+K_2O) \leq 20$, wherein the content of $Fe_2O_3$ is 0.5 percent by mass or less, and the content of ZnO is 2 percent mass or less, a temperature difference ΔT obtained by subtracting a devitrification temperature from a working temperature of the glass base material is 0° C. to 200° C. to suppress devitrification during glass formation, and wherein the glass flake is homogeneous and free from crystallized agglomerates.

17. The coated glass flake of claim 15 further comprising:
 a coating that covers a surface of the glass flake, the coating having a main component of metal or metal oxide.

18. The coated glass flake of claim 16 further comprising:
 a coating that covers a surface of the glass flake, the coating having a main component of metal or metal oxide.

* * * * *

UNITED STATES PATENT AND TRADEMARK OFFICE
CERTIFICATE OF CORRECTION

PATENT NO. : 9,237,994 B2
APPLICATION NO. : 13/058090
DATED : January 19, 2016
INVENTOR(S) : Kosuke Fujiwara and Akihiro Koyama Page 1 of 1

It is certified that error appears in the above-identified patent and that said Letters Patent is hereby corrected as shown below:

In the Claims col. 27, claim 3, line 6, delete the "," after the word "material" as follows:
glass base material "," is the temperature Signed and Sealed this
Twenty-sixth Day of July, 2016

Michelle K. Lee
*Director of the United States Patent and Trademark Office*